US006241677B1

(12) United States Patent
Guracar et al.

(10) Patent No.: US 6,241,677 B1
(45) Date of Patent: Jun. 5, 2001

(54) METHOD AND APPARATUS FOR ULTRASOUND IMAGE QUANTIFICATION

(75) Inventors: Ismayil M. Guracar, Redwood City; Samuel H. Maslak, Woodside; John W. Allison, Sunnyvale; Paul E. Chandler, Santa Cruz; John I. Jackson, Menlo Park; Arvind Jain, San Jose; Laurence S. McCabe, Sunnyvale, all of CA (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/478,662

(22) Filed: Jan. 6, 2000

Related U.S. Application Data

(62) Division of application No. 08/753,999, filed on Dec. 4, 1996.

(51) Int. Cl.[7] .................................................. A61B 8/00
(52) U.S. Cl. ............................................ 600/453; 600/455
(58) Field of Search .................................. 600/447, 437, 600/455, 454, 449

(56) References Cited

U.S. PATENT DOCUMENTS

| 4,067,236 | 1/1978 | Hottinger . |
| 4,103,679 | 8/1978 | Aronson . |
| 4,265,126 | 5/1981 | Papadofrangakis et al. . |

(List continued on next page.)

FOREIGN PATENT DOCUMENTS

| 0 838 288 A1 | 8/1990 | (EP) . |
| 0 222 913 B1 | 10/1990 | (EP) . |
| 0 415 324 B1 | 3/1991 | (EP) . |
| 0 520 338 A2 | 12/1992 | (EP) . |
| 2-126835 | 5/1990 | (JP) . |
| H6-217976 | 8/1994 | (JP) . |
| WO 86/00516 | 1/1986 | (WO) . |
| WO 90/02517 | 3/1990 | (WO) . |
| WO 91/15999 | 10/1991 | (WO) . |
| WO 92/07514 | 5/1992 | (WO) . |
| WO 92/10135 | 6/1992 | (WO) . |

OTHER PUBLICATIONS

Doppler Ultrasound, Physics, Instrumentation, And Clinical Applications, John Wiley & Sons, 1989, Chapter 11, pp. 188–205.
*Time Domain Formulation Of Pulse–Doppler Ultrasound And Blood Velocity Estimation By Cross–Correlation*, O. Bonnefous And P. Pesque, 1986, pp. 73–85.
Angle Independent Doppler Color Imaging: Determination Of Accuracy And A Method Of Dispaly, Ding–Yu Fei Et Al., Ultrasound In Med. & Biol., vol. 20, No. 2, 1994, pp. 147–155.

(List continued on next page.)

*Primary Examiner*—Marvin M. Lateef
*Assistant Examiner*—Maulin Patel
(74) *Attorney, Agent, or Firm*—Craig A. Summerfield, Esq.; Brinks Hofer Gilson & Lione

(57) ABSTRACT

A method and apparatus for quantifying and displaying ultrasound signals in an ultrasonic system are provided. A first signal value for each of at least one spatial location in a region of interest is acquired at a first time, and the signal values are summed to obtain a first surface integral value. A second signal value for each of said at least one spatial location in said region of interest is acquired at a second time, and the second signal values are summed to obtain a second surface integral value. The first surface integral value is summed with the second surface integral value to obtain a time based integral. The time based integral is displayed. Other quantities based on any of various ultrasound parameters, such as Doppler energy, Doppler velocity and B-mode intensity, are calculated and displayed as quantities or as waveforms as a function of time. Furthermore, various comparisons of quantities and waveforms are provided. Image plane data or other ultrasound data are used in the calculations. Finally, a histogram data structure is provided to aid calculation of the various quantities.

9 Claims, 16 Drawing Sheets

U.S. PATENT DOCUMENTS

| | | |
|---|---|---|
| 4,373,533 | 2/1983 | Linuma . |
| 4,476,874 | 10/1984 | Taenzer et al. . |
| 4,509,526 | 4/1985 | Barnes et al. . |
| 4,790,322 | 12/1988 | Linuma . |
| 4,800,891 | 1/1989 | Kim . |
| 4,873,985 | 10/1989 | Nakajima . |
| 4,928,698 | 5/1990 | Bonnefous . |
| 5,010,528 | 4/1991 | Ohtsuki et al. . |
| 5,014,710 | 5/1991 | Maslak et al. . |
| 5,062,427 | 11/1991 | Seo et al. . |
| 5,063,931 | 11/1991 | Leavitt . |
| 5,165,413 | 11/1992 | Maslak et al. . |
| 5,195,521 | 3/1993 | Melton, Jr. et al. . |
| 5,224,481 | 7/1993 | Ishihara et al. . |
| 5,233,994 | 8/1993 | Shmulewitz . |
| 5,235,984 | 8/1993 | D'Sa . |
| 5,241,473 | 8/1993 | Ishihara et al. . |
| 5,280,787 | 1/1994 | Wilson et al. . |
| 5,287,753 | 2/1994 | Routh et al. . |
| 5,322,067 | 6/1994 | Prater et al. . |
| 5,471,990 | 12/1995 | Thirsk . |
| 5,505,204 * | 4/1996 | Picot et al. ............................ 600/447 |
| 5,515,857 | 5/1996 | Tsujino et al. . |
| 5,538,003 | 7/1996 | Gadonniex et al. . |
| 5,555,534 | 9/1996 | Maslak et al. . |
| 5,623,930 * | 4/1997 | Wright et al. ......................... 600/447 |
| 5,675,554 | 10/1997 | Cole et al. . |
| 5,769,079 * | 6/1998 | Hossack et al. ..................... 600/454 |
| 5,800,356 | 9/1998 | Criton et al. . |
| 5,953,439 * | 9/1999 | Ishihara et al. ...................... 382/107 |

OTHER PUBLICATIONS

Quantative Measurement Of Volume Flow Rate (Cardiac Output) By The Multibeam Doppler Method, H. Tsujino Et Al., Medical Systems Division, Toshiba Corporation, Roshiba Medical Engineering Corporation, 1995, pp. 621–630.

Fractional Moving Blood Volume: Estimation with Power Doppler U.S. Jonathan M. Rubin et al., Radiology, Oct. 1995, pp. 183–190.

Toshiba Systems Data No. MSDUS0007EA Ultrasound Diagnostic System Powervision™ SSA–380 (1994).

Toshiba How to measure cardiac output accurately within just seconds. (Date Unknown).

National Cancer Institute—Grant Application R01 CA55076–02, Jul. 8, 1993.

Approximate Quantification of Detected Fractional Blood Volume and Perfusion From 3–D Color Flow and Doppler Power Signal Imaging, Paul L. Carson et al., 1993 Ultrasonics Symposium, IEEE pp. 1023–1026.

The dependence of myocardial ultrasonic intgrated backscatter on contractile performance, Samuel A. Wickline et al., Circulation 72, No. 1, Jul., 1985.

A Real–Time Integrated Backscatter Measurement System for Quantitative Cardiac Tissue Characterization, Lewis J. Thomas, III et al., IEEE Transactions on Ultrasonics, Ferroelectrics and Frequency Control, vol. UFFC–33, No. 1, Jan. 1986 (1985).

Ultrasound Integrated Backscatter Tissue Characterization of Remote Myocardial Infraction in Human Subjects, Zvi Vered et al., JACC vol. 13, No. 1 Jan. 1989; 84–91.

Ultrasonic Tissue Characterization With a Real Time Integrated Backscatter Imaging System in Normal and Aging Human Hearts, Tohru Masuyama et al., JACC vol. 14, No. 7, Dec. 1989; 1702–8.

Maternal and fetal haemodynamics in hypertensive pregnancies during maternal treatment with intravenous hydralazine or labetalol, Ann Harper et al., British Journal of Obstetrics and Gynaecology, vol. 98, No. 5, May 1991, pp. 453–459.

Laser Doppler imaging of axial and random pattern flaps in the maxillo–facial area. A preliminary report, Wolfgang Eichhorn et al., Journal of Cranio–Maxillo–Facial Surgery, vol. 22, No. 5, Oct. 1994, pp. 301–306.

Indication of Doppler Sampling on the Video Image of a Linear Scanner Without Modification of Commercial Equipment, Knut Matre et al., Ultrasound in medicine biology,vol. 11, No. 4, Jul./Aug. 1985, pp. 585–589.

Usefulness and Limitations of Digital Echocardiography in Detecting Wall Motion Abnormally During Stress Echocardiography in Detecting Wall Motion Abnormally During Stress Echocardiography, Jun Koyama et al., Jpn J Med Ultrasonics vol. 21, No. 11, (1994), pp. 695–701.

Visualizing Tumor Blood Flow by 3–Dimensional Color Doppler Ultrasound.

Arterial Wall Tissue Characterization by Analysis of Railo Frequency Signal Using Intravascular Ultrasound, Y. Takano et al., jpn J Med Ultrasonics vol. 21, No. 2 (1994), pp. 84–89.

An On–Line Computer Analysis of Exercise Capacity Using Continous Wave Doppler Flowmetry, H. Komura, Jpn J Med Ultrasonic vol. 20, No. 6 (1993) pp.

Experimental and Clinical Study of Tissue Characterization of Prostate using Amplitude Image and Mean Frequncy Image, Akifumi Yamane, Jpn J Ultrasonics vol. 20, No. 6, (1993), pp. 362–367.

Telemetry of Human Gastric Temperature with Quartz Crystal Resonator Using Ultrasonic Detection, The Japanese Journal of Medicine Instrumentation, vol. 60, No. 7 (1990), pp. 309–314.

Title Unknown, author unknown, Ika Kikai Gaku, vol. 57, No. 2, (1987), pp. 78–83.

Determination of Blood Flow Volume of Skin by Laser Dopler Method–Development of a New Data Analysis System, H. Sugihara et al., Ika Kikai Gaku, vol. 62, No. 10 (1992), pp. 470–474.

Tosbee Compact, Easy–to–operate Diagnostic Ultrasound System, K. Hara, Tishiba Review, vol. 46, No. 2, (1991), pp. 96–10.

Fully Digital Ultrasound Diagnostic System, K. Okubo et al., Tishiba Review, vol. 49, No. 2 (1994), pp. 84–88.

* cited by examiner

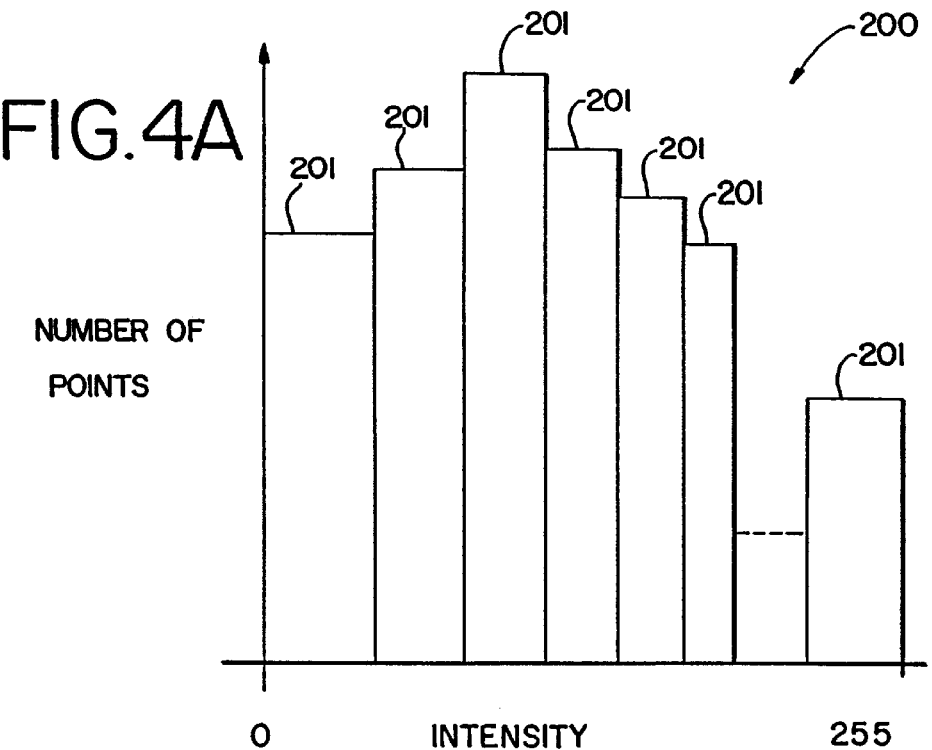
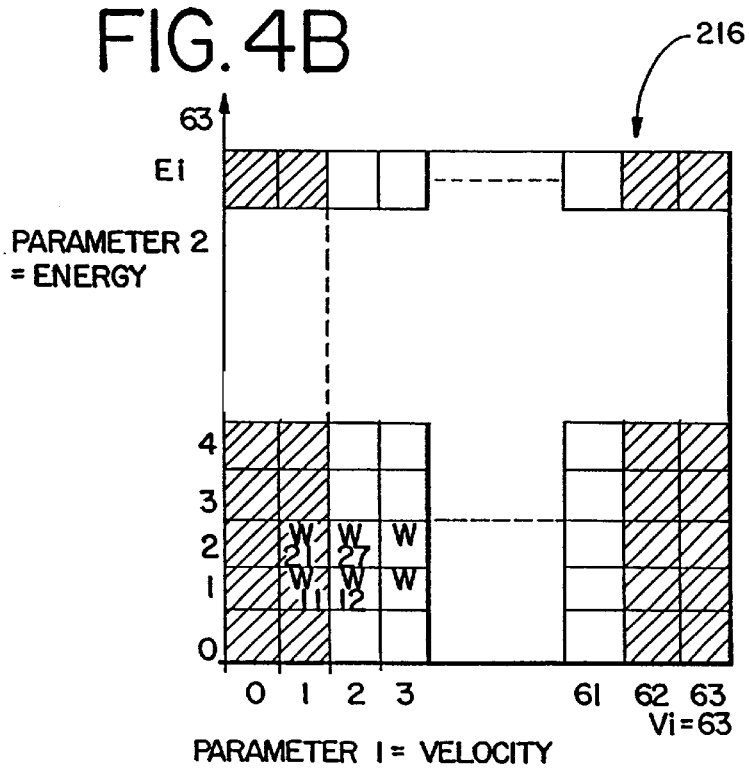
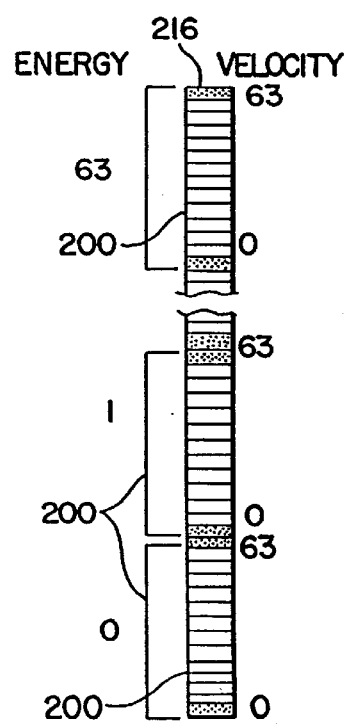

FIG.6A
$$E_{NSI} = \frac{\sum_{i}^{ROI} D(E_i)\, T_i(E_i, V_i)}{\sum_{i}^{ROI} T_i(E_i, V_i)}$$
WHERE  D = FUNCTION TO REVERSE LOG COMPRESSION
T = FUNCTION TO THRESHOLD
$E_i$ = DOPPLER ENERGY MEASUREMENT AT A PARTICULAR SPATIAL LOCATION WITHIN THE ROI
$V_i$ = DOPPLER VELOCITY MEASUREMENT AT A PARTICULAR SPATIAL LOCATION WITHIN THE ROI
$E_{NSI}$ = NORMALIZED SURFACE INTEGRAL
FIG.6B
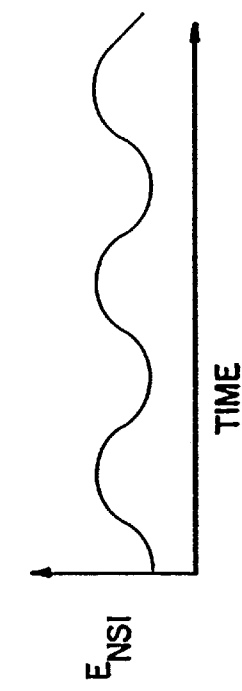
FIG.6C
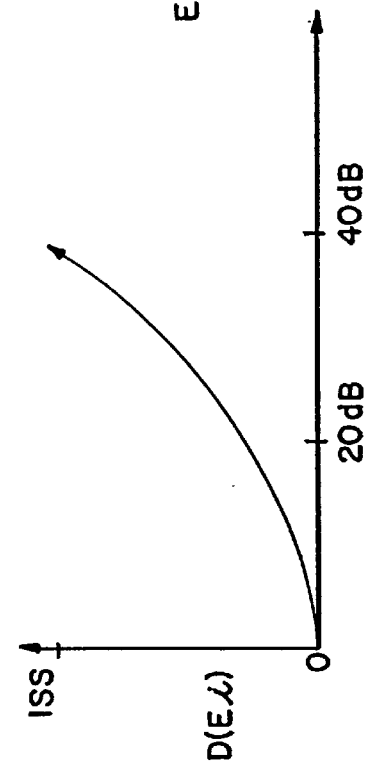

FIG.7
$$E_{TNSI}(n) = \sum_{t=T_{n-1}}^{t=T_n} E_{NSI}(t)$$
FIG.8A
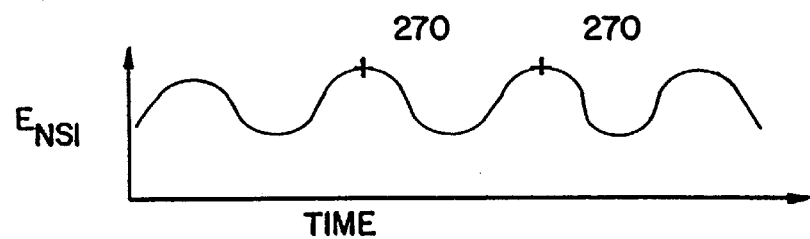
FIG.8B
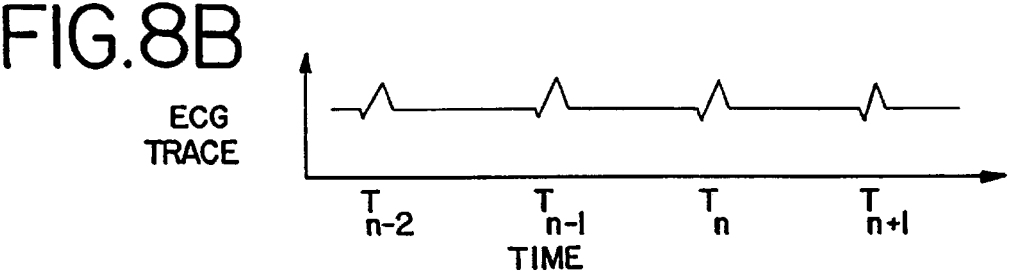
FIG.9
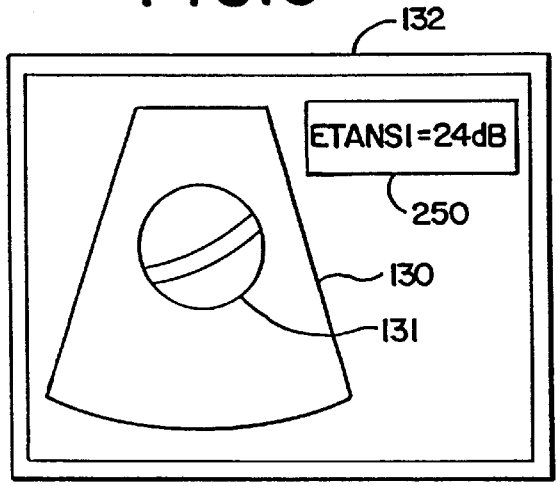
FIG.10
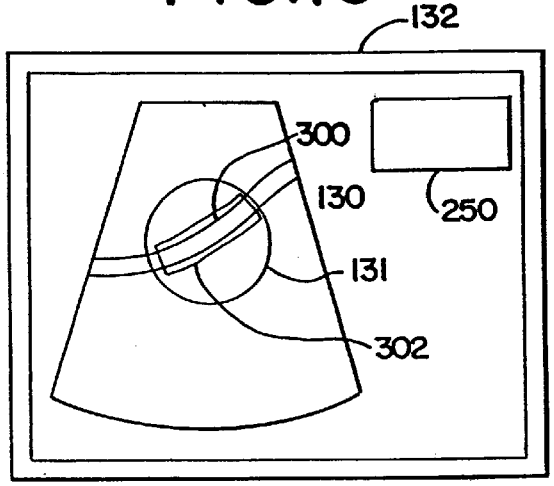

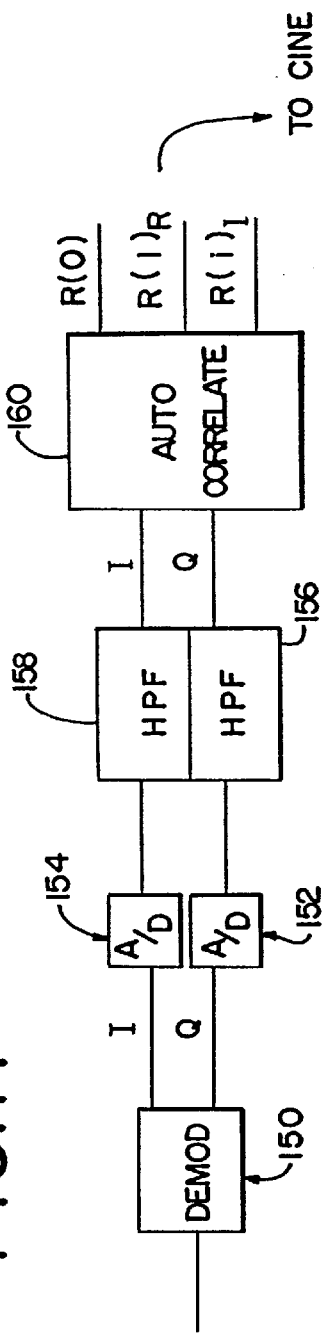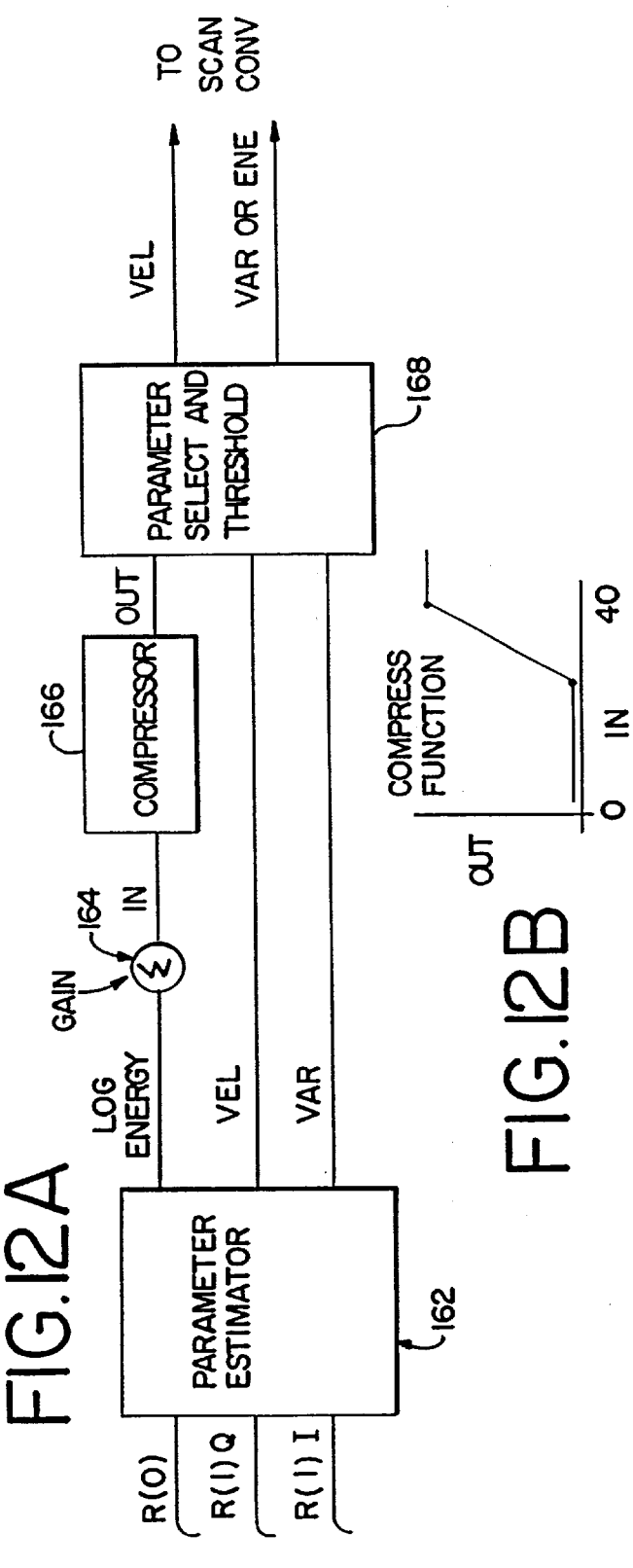

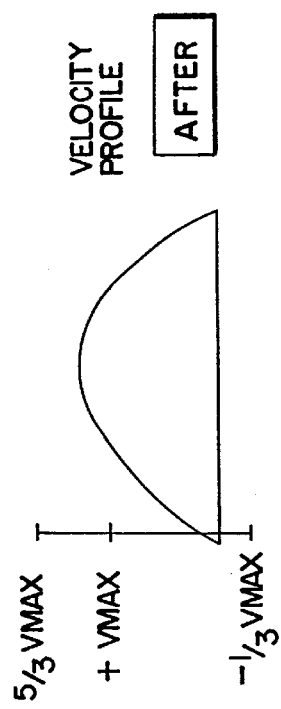
FIG.14A
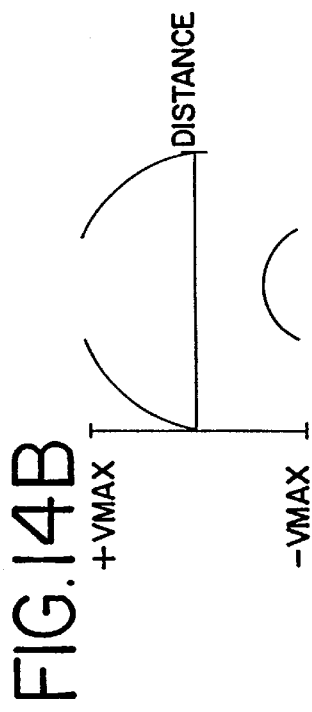
FIG.14B
FIG.14E
FIG.14D
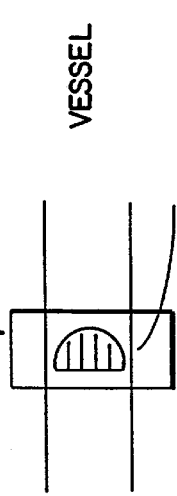
FIG.14C

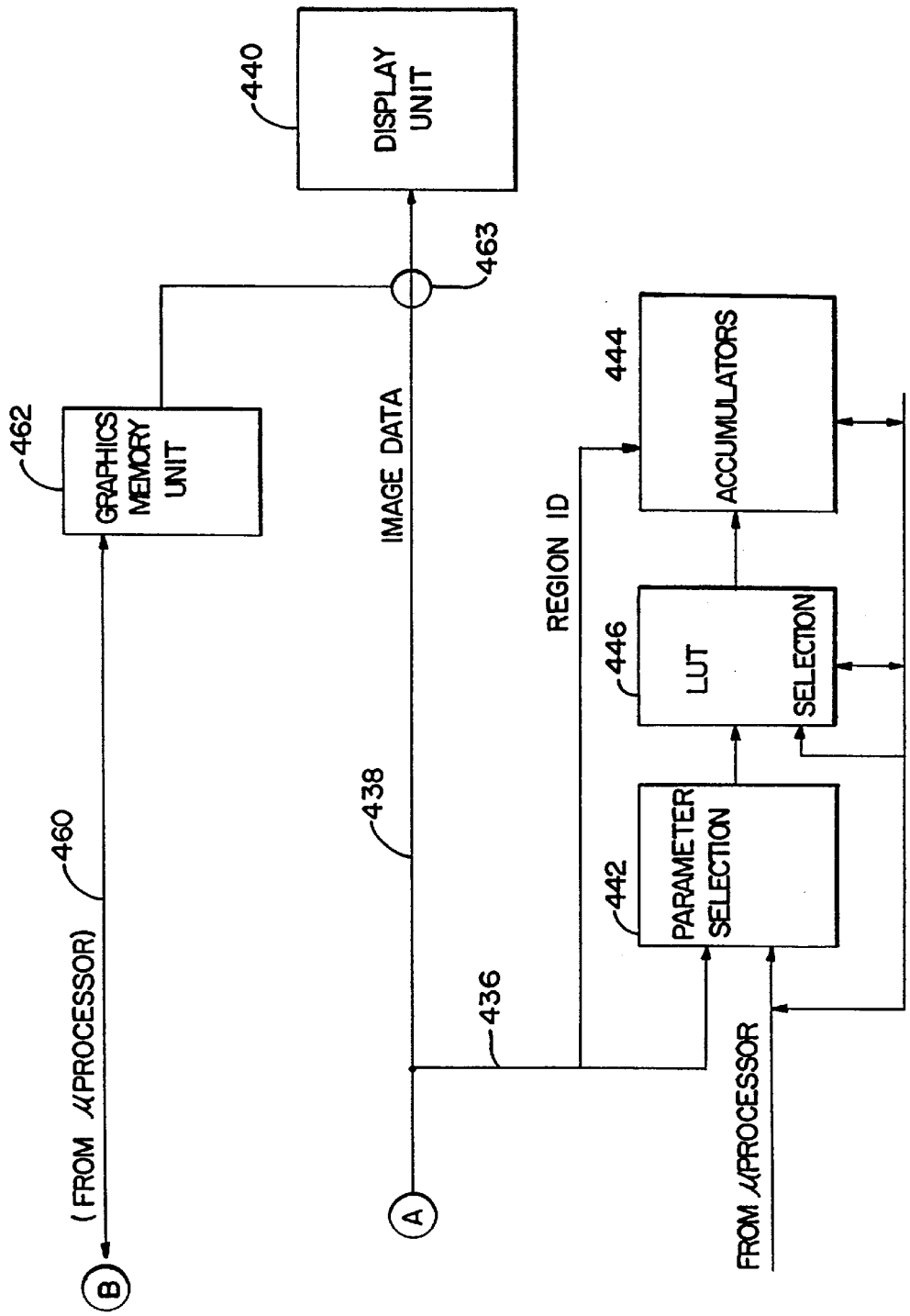

METHOD AND APPARATUS FOR ULTRASOUND IMAGE QUANTIFICATION

This application is a division of application Ser. No. 08/753,999, filed Dec. 4, 1996, (pending).

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

This application includes one microfiche appendix. The appendix contains 1 microfiche with 36 frames.

FIELD OF THE INVENTION

This invention relates in general to ultrasound systems and in particular to quantification, display and other uses of various parameter data, including surface and time integral data, in ultrasound systems.

BACKGROUND OF THE INVENTION

In traditional ultrasound imaging and display, color Doppler imaging (CDI), spectral Doppler imaging (SD), or B-mode imaging are available. CDI refers to color Doppler F-mode imaging techniques. CDI provides a qualitative evaluation of fluid dynamics and tissue motion in a body that is imaged. Thus, CDI techniques currently provide the user with limited quantitative information. B-mode imaging, with the associated gray-scale display, also provides a qualitative display with limited quantitative information. SD, on the other hand, provides the user with information about a single point or position in space. SD provides flow information as a display of the brightness of the spectrum and a velocity scale display.

Quantitative calculation of a surface integral or area average for a particular region of interest provides a measurement-based calculation—Doppler energy or power related to the amount of blood in a cross-sectional area or volume of tissue in the body. "Approximate Quantification Of Detected Fractional Blood Volume And Perfusion From 3-D Colorflow And Doppler Power Signal Imaging" by Carson et al., 1993 Ultrasonics Symposium, pp. 1023–26 discusses such a calculation. The article by Carson et al. discloses a signal power-weighted color pixel density calculated by summing the Doppler energy for the various pixels in the region of interest and dividing by the number of such pixels.

Limited use of linearization of B-mode data to aid in quantification is known. In U.S. Pat. No. 5,235,984 to D'Sa, a method for undoing the log compression and other processing to generate a linearized average of B-mode intensity in a region of interest is disclosed. D'Sa discloses averaging B-mode intensity for a region of interest and then linearizing the average B-mode intensity value. The quantified B-mode data is displayed. D'Sa also teaches a display of multiple B-mode intensity curves from sequential trace operations at one or more regions of interest.

Other techniques to aid quantification of Doppler velocity are known. One way to acquire Doppler velocity information and process the Doppler velocity information is by a one-dimensional histogram. The Doppler velocity histogram may then be displayed on an ultrasound display with the color display.

The color display of Doppler data is controlled by application of a threshold. Once color Doppler data of a particular parameter is obtained, the data is mapped to a color display. Before mapping, a threshold for the same particular parameter is applied to the data so that only data with a value above the threshold remains. Thus, the thresholded values are used for any calculations.

None of the ultrasound systems for obtaining and displaying ultrasound data is entirely satisfactory. As discussed above, only limited quantification is known. It is therefore desirable to provide an improved ultrasound system for obtaining and displaying ultrasound data.

SUMMARY OF THE INVENTION

The invention provides an efficient method for processing and displaying various ultrasound data. In one aspect, a method and apparatus for quantifying and displaying Doppler signals in an ultrasonic Doppler system are provided. A first Doppler signal value for each of at least one spatial location in a region of interest is acquired at a first time, and the Doppler signal values are summed to obtain a first surface integral value. A second Doppler signal value for each of said at least one spatial location in said region of interest is acquired at a second time, and the second Doppler signal values are summed to obtain a second surface integral value. The first surface integral value is summed with the second surface integral value to obtain a time based integral. The time based integral is displayed. In another aspect of the invention, the time based integral is normalized by the number of surface integrals summed.

In another aspect of the invention, a method and apparatus for displaying multiple quantities obtained at different times from data corresponding to a region of interest are provided. The region of interest is selected and includes at least one spatial location. First and second ultrasound signal values for each of said at least one spatial location are acquired at first and second times, respectively. Comparison data are created as a function of said first and second ultrasound signal values and displayed.

In yet another aspect of the invention, a method and apparatus for displaying multiple quantities obtained at the same or different times from data corresponding to multiple regions of interest are provided. First and second regions of interest are selected to include at least a first and second spatial location, respectively. First and second ultrasound signal values are acquired for each of the first and second spatial locations. The second ultrasound signal value is derived from the same type of ultrasound parameter as the first ultrasound signal value. Comparison data are created as a function of the first and second ultrasound signals and displayed.

In another aspect of the invention, a method and apparatus for displaying multiple quantities obtained from data corresponding to different regions of interest are provided. First and second regions of interest are selected. First and second ultrasound signal values are obtained for said first and second region of interests. The second ultrasound signal value is derived from a different type of ultrasound parameter than the first ultrasound signal value. Comparison data are created as a function of said first and second ultrasound signals.

In yet another aspect of the invention, a method and apparatus for displaying multiple quantities obtained from a region of interest are provided. A region of interest is selected, and a B-mode intensity associated with said region of interest is obtained. Further, an ultrasound signal value selected from the group of Doppler energy and Doppler velocity is also obtained. Comparison data are created as a function of said B-mode intensity and said ultrasound signal value.

In another aspect of the invention, a method and apparatus for displaying multiple results obtained from a region of interest are provided. A region of interest is selected, and a Doppler velocity and energy associated with the region of interest are obtained. Comparison data are created as a function of the Doppler velocity and Doppler energy and displayed.

In another aspect of the invention, a method and apparatus for providing flow quantities data by thresholding are provided. A Doppler energy and velocity for each of multiple spatial locations in a region of interest are acquired at a first time. A threshold is applied to the Doppler energies based on the Doppler velocities to obtain remaining Doppler energies. The remaining Doppler energies are summed to obtain a surface integral energy value.

In another aspect of the invention, a method and apparatus for deriving a quantity with a histogram are provided. An ultrasound signal value selected from the group of Doppler energy and Doppler variance is acquired for each of multiple spatial locations in a region of interest. The histogram includes multiple bins corresponding to bin ultrasound signal values. The counts in the appropriate bins are incremented based on the acquired ultrasound signal values, and a quantity is derived from the histogram. In yet another aspect of the invention, the histogram is displayed without deriving a quantity.

In another aspect of the invention, a method and apparatus for deriving a quantity based on a threshold are provided. Ultrasonic signal values for multiple spatial locations in a region of interest are acquired. A histogram is created based on the values. The threshold is applied to the histogram, and a quantity is derived from the histogram after applying the threshold.

In yet another aspect of the invention, a method and apparatus for using data in an ultrasound system over time to derive a quantity are provided. First ultrasonic signal values for multiple spatial locations in a region of interest are acquired at a first time and used to create a histogram. Second ultrasonic signal values, derived from the same type of ultrasound parameter as the first ultrasound values, are acquired for the multiple spatial locations in the region of interest at a second time. A second dimension of the histogram is created as a function of the second ultrasound values. A quantity is derived from the histogram.

In another aspect of the invention, a method and apparatus for setting the integration interval for time integrated surface integrals are provided. At least first and second ultrasound signal values for each of multiple spatial locations in a region of interest are acquired at first and second times, respectively. At least said first and second Doppler signal values are summed to obtain at least first and second surface integral values, respectively. A time period is selected from a waveform comprising at least first and second times corresponding to the first and second surface integral values. The surface integrals within the selected time period are summed to obtain said time integrated surface integral.

In another aspect of the invention, a method and apparatus for adjusting a color image on an ultrasound display are provided. A region of interest is selected in an ultrasound image display having at least two dimensions. A controller assigns an area of color measurement and display to encompass the region of interest, and a color image is mapped onto the display for the area.

In yet another aspect of the invention, a method and apparatus for automatically detecting a border without altering data for performing a calculation for a region of interest are provided. A region of interest associated with an ultrasound image display having at least two dimensions is selected. A first ultrasound value for each of multiple spatial locations in the region of interest is obtained. A threshold is applied to the first ultrasound values to detect a border within the region of interest. A calculation is performed to derive a surface integral of the first ultrasound values within the border including the first ultrasound values that are below and above the threshold. In yet another aspect of the invention, a second type of ultrasound signal value is used to derive the surface integral.

In yet another aspect of the invention, a method and apparatus for quantifying and displaying Doppler signal strength signals associated with a point or line are provided. Color values based on image plane data representative of different Doppler signal strengths are mapped at multiple spatial locations. A color Doppler signal strength display is created based on said color values, and a point or line is selected. A Doppler signal strength value associated with the point or line is obtained from the image plane data. A quantity derived from said Doppler signal strength value or values is displayed. In a further aspect of the invention, an area is selected. The values are obtained prior to color mapping, and the displayed quantity is derived from the values.

BRIEF DESCRIPTION OF THE DRAWINGS

FIGS. 1A and 1B will be referred to as FIG. 1 below, when reference is to the composite.

FIG. 4A is a graphical representation of a one-dimensional histogram.

FIG. 4B is a graphical representation of a two-dimensional histogram.

FIG. 4C is another graphical representation of a two-dimensional histogram for use by a microprocessor.

FIG. 6A is a mathematical representation of a normalized surface integral of Doppler energy.

FIG. 6B is a graphical representation of the normalized surface integral of Doppler energy of FIG. 6A plotted over time.

FIG. 6C is a graphical representation of the reverse log compression function.

FIG. 7 is a mathematical representation of a time integral of the normalized surface integral of Doppler energy.

FIG. 8A is a graphical representation of the normalized surface integral of Doppler energy plotted over time and displayed on the ultrasound system for time period selection.

FIG. 8B is a graphical representation of an ECG trace for display on the ultrasound system.

FIG. 9 is a schematic view of a two-dimensional ultrasound image on the display unit of FIG. 1B with a box for display of calculations and waveforms.

FIG. 10 is a schematic view of a two-dimensional ultrasound image on the display unit of FIG. 1B or FIG. 15B with automatic region of interest determination and a box for display of calculations and waveforms.

FIG. 11 is a block diagram of the F-mode processor of FIG. 1A.

FIG. 12A is a block diagram of the parameter estimator of FIG. 1A.

FIG. 12B is a graphical representation of a log compression function.

FIG. 14A is a schematic view of a vessel on a two-dimensional ultrasound display showing a region of interest and a flow profile for the region of interest.

FIG. 14B is a graphical representation of the velocity profile of FIG. 14A sensed by ultrasound system before baseline shifting.

FIG. 14C is a graphical representation of a histogram created from the velocity profile of FIG. 14B.

FIG. 14D is a graphical representation of the histogram of FIG. 14C after baseline shifting.

FIG. 14E is a graphical representation of the velocity profile of FIG. 14B after baseline shifting.

FIGS. 15A, 15B together form a block diagram of an alternative ultrasound system for calculating various quantities. FIGS. 15A and 15B will be referred to as FIG. 15, where reference is to the composite.

DETAILED DESCRIPTION OF PREFERRED EMBODIMENTS

Definitions:

Surface integral: the sum of values associated with a set of data corresponding to a two-dimensional slice of a body.

Mapping: obtaining a second value from a table based on a first value.

Parameters: any of various ultrasonic signal measurements, such as energy, velocity, variance or B-mode intensity.

Image plane data: ultrasonic information in a raster grid. Referring now to FIGS. 1 and 15, ultrasound systems 100, 400 for acquiring ultrasound data and displaying the data are shown. FIG. 1 illustrates one of the preferred embodiments of the invention. Generally, ultrasound systems such as the Acuson 128XP or the system disclosed in U.S. application Ser. No. 08/620,283, filed on Mar. 22, 1996, the disclosure of which is herein incorporated by reference, can be used for ultrasound system of FIG. 1, supplemented with the image quantification features described below.

FIG. 15 illustrates another one of the preferred embodiments of the invention. Generally, ultrasound systems such as the Acuson Sequoia™ or Aspen™ systems or the system disclosed in U.S. application Ser. No. 08/432,858, filed on May 2, 1995, the disclosure of which is herein incorporated by reference, can be used for the ultrasound system of FIG. 15, supplemented with the image quantification features described below.

In either system, image plane data is used to calculate various quantities. In the system of FIG. 1, a microprocessor 127 acquires image plane data to perform various calculations. Preferably, the microprocessor 127 is a TMS 320C25 by Texas Instruments. In the system of FIG. 15, look-up tables 446 and accumulators 444 acquire image plane data to perform various calculations. Acoustic data or color values may also be used to calculate any of the various quantities.

Figure 1A:
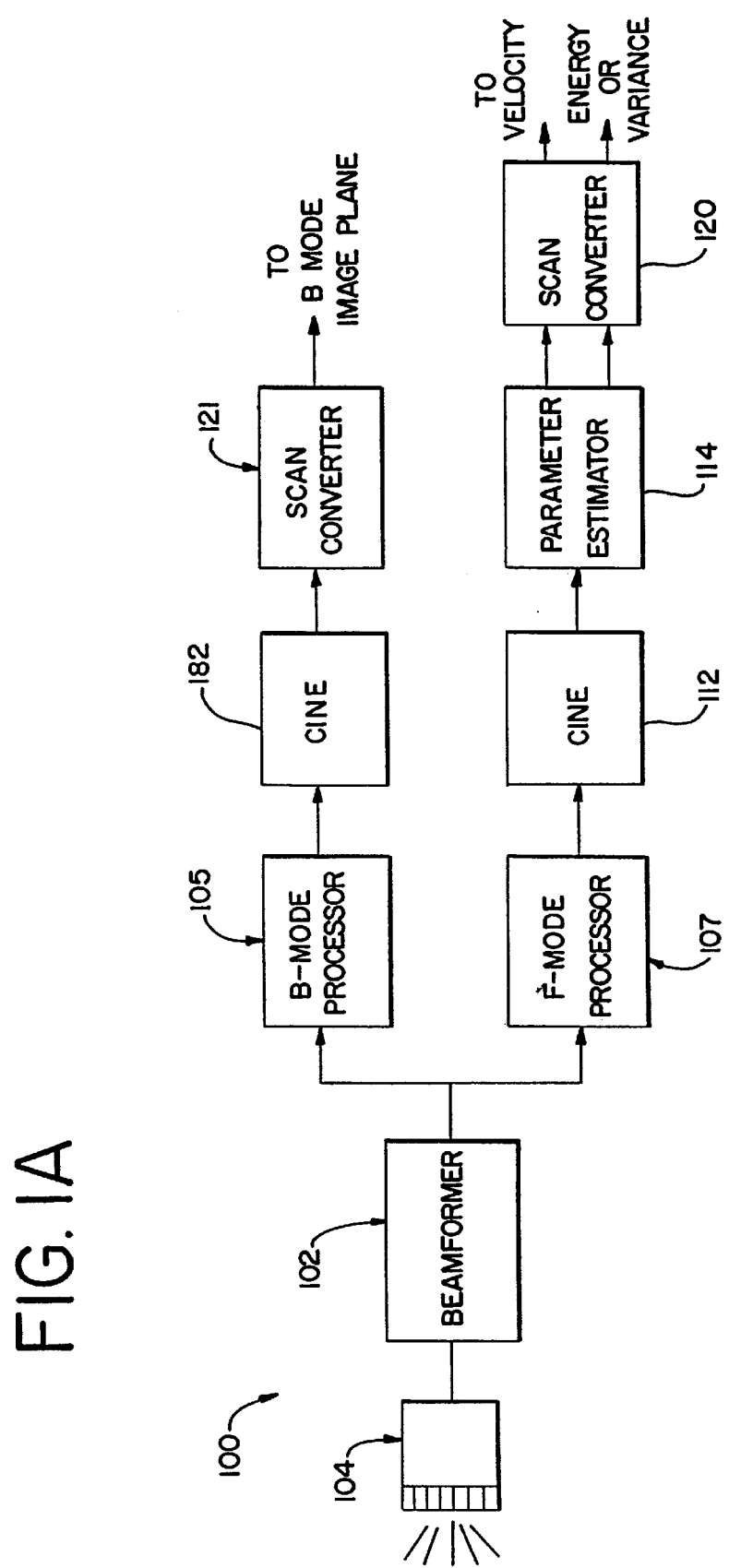
FIGS. 1A and 1B form a block diagram of an ultrasound imaging system that incorporates a preferred embodiment of the present invention.
Figure 15A:
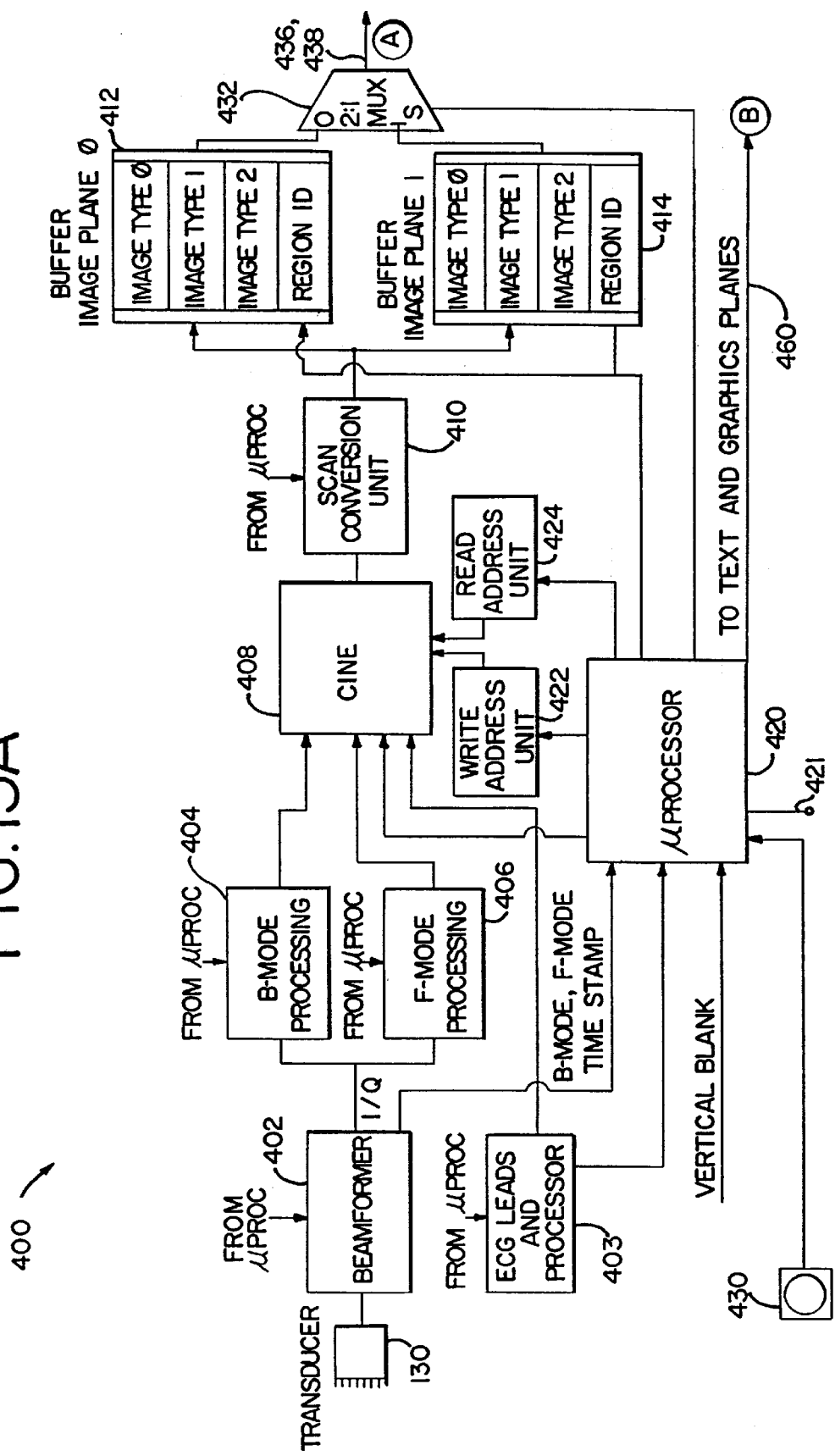

Image plane data is created by applying signals to a body, detecting echo signals and processing the echo signals. Referring to FIG. 1A, the ultrasound system 100 includes a transducer 104 connected to a beamformer 102. Beamformer 102 applies appropriate signals to the transducer 104, to cause the transducer 104 to transmit ultrasound signals towards a body. Referring to FIG. 15A, a beamformer 402 generates similar signals for transmission by a transducer 430. Generally, the discussion below refers to the embodiments of both FIG. 1 and FIG. 15 simultaneously.

The transducers 104, 430, scan a region in a body to be imaged with ultrasound signals in one of several possible formats, such as linear, steered linear, sector, VECTOR® and curved linear array formats. The ultrasound signals are transmitted sequentially along scan lines (not shown) spanning a scan plane in a region of interest. Portions of the ultrasound signals echo off structures and fluids within the body.

The transducer 104, 430 detects the echoes, and the detected echo signals are output to the beamformer 102, 402. The beamformer 102, 402 processes the signals as known in the art.

The output of the beamformer 102, 402 is further processed by a B-mode processing unit 105, 404 and an F-mode processing unit 107, 406. These two units operate in parallel. For the sake of simplicity, the B-mode processing unit 105 and F-mode processing unit 107 of the embodiment shown in FIG. 1 are described below. The B-mode processing unit 404 and F-mode processing unit 406 of the embodiment shown in FIG. 15 operate similarly.

B-mode processing unit 105 provides data for creating a gray-scale B-mode intensity image, which is generally indicative of echo signals from structure. The overall function of the B-mode processing unit 105 is to demodulate the signal from beamformer 102 and to provide a compressed digital output.

Figure 13A:
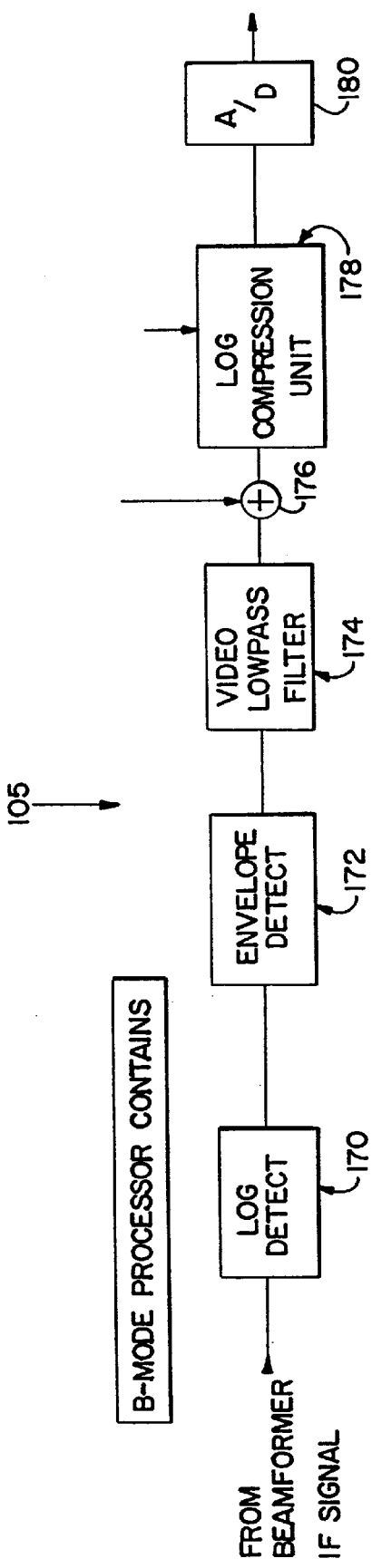
FIG. 13A is a block diagram of the B-mode processor of FIG. 1A.

Referring to FIG. 13A, the B-mode processing unit 105 includes a log detection unit 170 that converts the input signal from the beamformer 102 to a log (dB) scale. Envelope detector 172 filters the log scale signal and outputs the envelope of the signal. Video low pass filter 174 removes further undesirable high frequency variations from the envelope signal. A gain unit 176 amplifies the low pass filtered envelope signal. The amount of gain provided by gain unit 176 is controlled by the system operator, who adjusts gain to alter the brightness of the B-mode intensity gray scale image displayed on display unit 132.

Figure 13B:
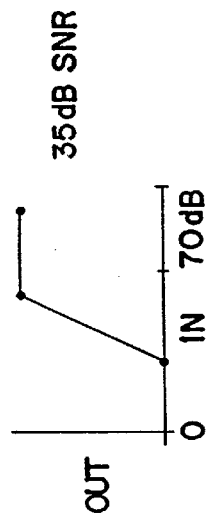
FIG. 13B is a graphical representation of a log compression function.

The B-mode processor unit 101 also includes a log compression unit 178 that compresses the gain adjusted signal. FIG. 13B illustrates the preferred log compression function applied by the log compression unit 178. The B-mode log compression function preferably depends on operator input from user interface 133, as known in the art. Finally, an A/D converter 180 converts the analog compressed signal to a digital signal. The B-mode processing unit 105 outputs digital B-mode intensity data on an acoustic grid (B-mode ultrasound signal values).

Referring back to FIG. 1, the F-mode processing unit 107 generates Doppler information from the analog output of the beamformer 102. Doppler information is derived from echo signals from moving reflectors.

Referring now to FIG. 1, the F-mode processing unit 107 is shown in detail. A demodulator 150 divides the echo signals into in-phase (I) and quadrature (Q) components, as known in the art. A/D converters 152, 154 convert the I and Q analog signals into digital signals. High pass filters 156, 158 remove wall or clutter from the digital signals. When tissue movement is imaged, the high pass filters 156, 158 may be bypassed. An auto-correlation unit 160 computes real and imaginary signals as a function of the auto-correlation of the I and Q filtered signals, as known in the art. A zero (0) to one (1) sample lag is used, and the resulting signals are referred to as the auto-correlation values $R(0)$, $R(1)_r$, $R(1)_i$. The $R(0)$, $R(1)_r$, $R(1)_i$ signals represent Doppler data. As an alternative embodiment, the Doppler data is acquired according to the time shift techniques described by Bonnefous in U.S. Pat. No. 4,928,698.

The Doppler and B-mode data from F-mode and B-mode processing units 107 and 105 is stored. Referring to FIG. 1, a CINE 112 stores the Doppler data from the F-mode processing unit 107. Preferably, the auto-correlation values are stored in unit 112. A separate CINE 182 stores the B-mode data from B-mode processing unit 105. The stored B-mode and Doppler data is retrievable for later playback.

Alternatively and referring to FIG. 15, a single CINE 408 stores data from both the B-mode processing unit 404 and F-mode processing unit 406. The reading and writing of image information into or out of memory 408 is controlled by microprocessor 420 employing a write address unit 422 and a read address unit 424. In the embodiment shown in FIG. 15, the F-mode processor 406 further processes the Doppler data to detect Doppler parameter information. Obtaining Doppler parameter information is discussed below with respect to FIG. 12.

An estimator unit 114 derives Doppler parameter information from the Doppler data in CINE 112. Doppler parameter information includes data for different types of parameters, such as energy, mean velocity, variance and acceleration values. Referring to FIG. 12A, the estimator unit 114 includes parameter estimator 162 that derives values for the Doppler parameters, as known in the art. For example, the energy value is equal to $R(0)$. The terms Doppler power and Doppler energy are used synonymously and are intended to refer generally to parameters that vary with the signal strength of a Doppler signal.

An estimator gain unit 164 amplifies the energy value. The amount of gain provided by estimator gain unit 164 depends on input from the operator of the ultrasound system 100. Gain adjustments alter the color corresponding to each Doppler energy value displayed on display unit 132.

Compressor 166 compresses the amplified energy value. FIG. 12B illustrates a preferred compression function which is dependent on the operator's control of the dynamic range. In particular, a toggle switch on user interface 133 provides operator input for selection of the output level. The operator changes the dynamic range, as known in the art, to alter the mapping of input energy values to the range of output values for eventual display. Alternatively, the ultrasound system 100 may be preprogrammed with a particular output level.

The parameter selection and threshold unit 168 applies thresholds to selected ones of the compressed energy values and the other output values of the parameter estimator 162. The level of any given threshold depends on operator input or programmed threshold levels. The programmed threshold levels are preferably selected as appropriate for particular applications of the ultrasound system 100. The thresholds are applied to any of Doppler velocity, variance or energy. Threshold values associated with one parameter may be used to threshold another parameter. For example, an energy threshold value is applied to energy values associated with a particular signal for setting velocity values corresponding to the same signal to zero. A threshold table is used to compare and to threshold the digital parameter values.

The parameter selection and threshold unit 168 also implements selection of various parameters, as known in the art. The selection is controlled by the operator via user interface 133. The selected parameter is output from estimator unit 114 for display and other processing. The output is an acoustic frame of data associated with a particular Doppler parameter, such as acoustic Doppler energy data. While one output line is shown for variance or energy, separate output lines for each parameter can be provided.

Referring to FIG. 1, the estimated parameters in acoustic frames are then scan converted to create frames of image plane data of Doppler ultrasound signal values. Scan conversion unit 120 converts the acoustic grid Doppler data to display grid Doppler data. The scan conversion unit 120 provides Doppler energy image plane data, Doppler velocity image plane data and any other Doppler parameter image plane data to buffer 123.

Likewise, the acoustic grid B-mode intensity data from CINE 182 is converted by a scan conversion unit 121. The B-mode intensity ultrasound signal values image plane data is also stored in buffer 123. B-mode image plane data, other than intensity, may be provided to and stored in buffer 123.

Referring now to the embodiment shown in FIG. 15, the B-mode intensity and Doppler ultrasound signal value data stored in CINE 408 is also scan converted and stored. A scan conversion unit 410 converts both the Doppler and B-mode acoustic data into image plane data. The image plane data is stored in buffers 412, 414, corresponding to image type 0 and image type 1, respectively.

Referring to both FIGS. 1 and 15, the image plane data in buffers 123, 412, and 414, along with any other image plane data, typically comprises the identity of pixels or spatial locations corresponding to particular areas of a body. The image plane data is divided into frames of image plane data. Each frame of image plane data contains data acquired from the body at a particular time. Each of the buffers 123, 412, 414 is divided into sections for storing frames of the different types of image plane data, such as B-mode intensity, Doppler energy, Doppler variance, or Doppler velocity. For any particular type of parameter, values for each spatial location are stored in buffers 123, 412, and 414.

While the scan converted data is written into buffers 123, 412, 414, other previously stored image plane data is retrieved from the buffers 123, 412, and 414. The image plane data is used to create a display on display unit 132, 440. The microprocessor 127, 420 controls storage and retrieval of the image plane data.

Referring to FIG. 15, image plane data is applied along signal path 438 to display unit 440 for displaying B-mode and Doppler images in a manner known to those skilled in the art. Generally, the B-mode and Doppler images are created as discussed below with reference to FIG. 1. Referring to FIG. 1, the B-mode or Doppler image plane data from buffer 123 is provided to color mapping unit 126. The color mapping unit 126 derives display information, such as RGB color values, therefrom for display as image 130 on the display unit 132. For color Doppler display, a color corresponding to the Doppler parameter value at any given pixel is selected for display. For gray scale B-mode display, a gray intensity corresponding to the B-mode intensity value at any given pixel is selected for display. Thus, the color values also represent ultrasound signal values.

The particular B-mode or Doppler image 130 displayed is a function of operator input. Operator selection of the type of image 130 is input with the user interface 133. Preferably, the user interface 133 comprises a QWERTY keyboard. The possible types of image 130 include a display of either Doppler parameters (such as velocity, velocity variance or energy), B-mode parameters (such as intensity), or a combination of parameters.

Figure 2:
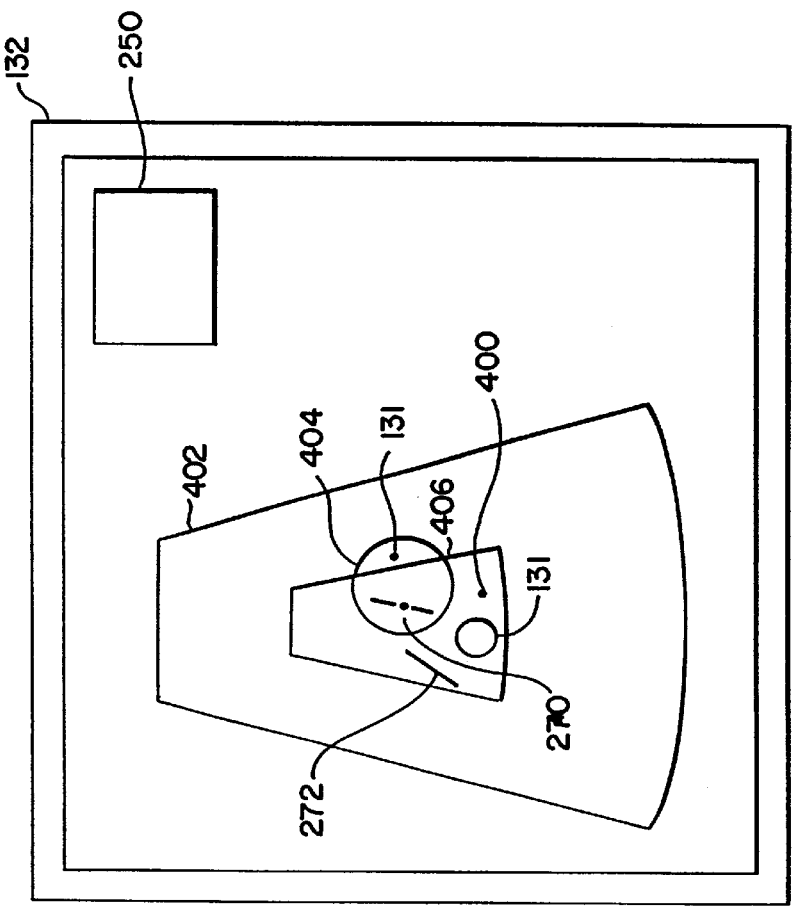
FIG. 2 is a schematic view of a two-dimensional ultrasound image on the display unit of the ultrasound system of FIGS. 1A and 1B or FIGS. 15A and 15B.

One combination of parameters includes a B-mode intensity image with a Doppler energy image displayed within the B-mode image. An example of such a display is shown in FIG. 2. A color Doppler image 400 overlays a B-mode image 402. The color Doppler image 400 represents the area of the body and area of the B-mode image 402 where Doppler echo signals are acquired and processed as discussed earlier. The shape of the color Doppler image 400 preferably conforms to the scan line format used. For spatial locations corresponding to both B-mode and Doppler information, a combined color value is selected. The combined color value is clipped to a maximum color value if the combined value is larger than the maximum color value. Alternatively, for each spatial location within image 130, either a Doppler value or a B-mode value is selected and mapped to a color or grey scale value, respectively.

Another combination display includes the color display of a image 130 of blended parameters. For example, the color mapping unit 126 applies a RAM based look-up table to map two parameters, such as Doppler energy and velocity. Doppler energy and velocity data for each pixel are mapped to values in the table of Doppler energy and velocity values and an output of a particular color is selected from the table. Thus, a velocity-energy image 130 is created.

Once the type of image 130 is selected, field control map 125 determines what image plane data from buffer 123 to use for the display for any given pixel. Preferably, field control map 125 is a memory device for prioritization of image data and for rejecting low velocities for velocity imaging. Field control map 125 controls overlaying of images 130. For example, a display of B-mode intensity with color Doppler energy overlaid is created. Typically, the field control map 125 uses the Doppler velocity image plane data to determine whether a particular pixel is associated with tissue or structure for display of the appropriate image plane data. One particular velocity value or any lower values are associated with tissue, while any higher velocities are associated with fluid. The particular tissue verses fluid velocity value depends on the operator control of the selectable velocity scale and filter, as known in the art. Field control map 125 then selects the appropriate image plane data from buffer 123, such as B-mode intensity data for a pixel associated with tissue and Doppler energy data for a pixel associated with fluid. Display of other combinations of ultrasound parameters and applying a threshold to parameters other than Doppler velocity are possible.

Real-time display derived from image plane data, alone or in combination with other data, is displayed on display unit 132. For example, a frame of real-time color mapped energy values displayed over a B-mode image is displayed followed by a frame of average energy values displayed over the B-mode image. This display process is then repeated for each new frame. The average data may be of any parameter and from any time period, including the two most immediately preceding real-time frames of image plane data. Further, any combination or no combination of real-time data with an average data or other calculated data may be displayed on display unit 132. The order of displaying frames may not correspond to the order in which the frames were acquired.

Other various combinations of display are possible. For example, a display derived from one frame of B-mode image plane data is frozen on the display unit 132 for one or several time periods while displays derived from multiple frames of Doppler image plane data are displayed over the B-mode display. As another example, the microprocessor 127 compares each frame of image plane data and retains the highest or lowest parameter value for each pixel. Thus, an accumulated frame of the highest or lowest parameter values over one or more time periods is created. The display is then derived from the accumulated frame. Other values, such as the mean value could also be retained.

Referring to FIG. 2, once the image 130 is displayed, a region of interest 131 is selected by the operator. Referring to FIGS. 1 and 2, as shown by block 127a in FIG. 1, the microprocessor 127 receives the input from the user interface 133 and controls the display unit 132 for selection of the region of interest 131. The operator selects the region of interest 131 from the image 130 on display unit 132. The operator manipulates the user interface 133, such as a track ball or other device known in the art. The operator positions icons to create a border for the region of interest 131, draws the region of interest 131 or designates a size and shape of the region of interest 131 around a positioned icon. The icon or drawing of the region of interest 131 is displayed on display unit 132 in real-time as the user manipulates user interface 133. Referring the FIG. 15, the microprocessor 420 controls the selection of the region of interest 131 as discussed above for microprocessor 127 (FIG. 1). Further, the operator may select multiple regions of interest 131 which may or may not overlap.

Referring to FIG. 2, the region of interest 131 as shown surrounds multiple spatial locations. As an alternative to selecting the region of interest 131 representing multiple spatial locations, the operator designates either a single point represented by icon 270, a line 272 or a volume as the region of interest. In this way, one or more spatial locations corresponding to the region of interest 131 are selected for further processing. For the sake of simplicity, the discussion below deals with an example where the region of interest 131 includes multiple spatial locations. Similar processing is performed whether the region of interest 131 comprises a single spatial location, multiple spatial locations corresponding to a line 272, multiple spatial locations corresponding to an area, or multiple spatial locations corresponding to a volume.

Referring to FIGS. 1 and 15, once the region of interest 131 is selected by the user, the microprocessor 127, 420 determines the spatial location address for each pixel within the region of interest 131. In the embodiment of FIG. 1, the address information is stored in the microprocessor 127. In the embodiment of FIG. 15, the address information is stored in the region Id buffer within the buffers 412, 414.

The discussion above generally explains the acquisition and display of ultrasound information. Either of the two embodiments disclosed above acquire the ultrasound information. Other systems and methods may also be used to acquire the ultrasound information. The discussion below explains the various uses and calculations for the ultrasound information. Many of the calculations and uses described below are new. For each region of interest 131, the ultrasound system 100, 400 has various types of parameter image plane data, such as Doppler energy data. The image plane data or any other ultrasound signal value data associated with spatial locations within any region of interest 131 are used for various calculations and display adjustments.

One such display adjustment avoids calculations based on unavailable data. Referring to FIG. 2, some spatial locations associated with the region of interest 131 are outside the border 406 of the color Doppler image 400. Doppler echo signals and associated image plane data for part of the region of interest 131 are not created. Any calculations for the region of interest 131 based on the Doppler image plane data do not account for the portion of the region of interest 131 outside of the color Doppler image 400.

Preferably, the region of interest 131 is within both the color Doppler image 400 and the B-mode image 402 and no further adjustments of the color Doppler image 400 are made. Where adjustment is needed, several alternative solutions are possible. First and referring to FIG. 1, the operator configures the ultrasound system 100 so that the region of interest 131 is the only area in the image 130 that Doppler image plane data is obtained and displayed. As known in the art, the microprocessor 127 controls the beamforner 102 and transducer 104 to obtain echo signals from particular locations. Echo signals are obtained for the spatial locations represented by the region of interest 131.

Alternatively and referring to FIG. 2, the color Doppler image 400 overlaying the B-mode image 402 is moved to encompass the region of interest 131. The microprocessor 127 controls movement of the color Doppler image 400 by comparing region ID data with Doppler image plane data associated with each spatial location. The center point of the region of interest 131 is aligned with the center point of the Doppler display 400 or the color Doppler image is moved toward any locations of the region of interest 131 not in the color Doppler image 400. If spatial locations in the region of interest 131 fall outside the color Doppler image 400 after movement, the microprocessor 127 increases the size of the color Doppler image 400. The size is increased until the color Doppler image 400 covers and the ultrasound system 100 acquires echo signals for every spatial location in the region of interest 131.

Movement of the color Doppler image 400 is preferable to obtaining Doppler image plane data for only the region of interest 131 as discussed above. Less processing is required if the color Doppler image 400 is shaped as a function of the scan line format instead of conformed to the region of interest 131. Thus, the color Doppler image 400 preferably has a wedge or other sector shape.

The microprocessor 127 also controls reduction of the size of the color Doppler image 400 to more closely conform to the size of the region of interest 131. First, the microprocessor 127 determines that every spatial location within the region of interest 131 or border 404 are within the area of color Doppler image 400. Second, the microprocessor 127 reduces the size of color Doppler image 400 by control of beamformer 102 and transducer 104. The size is reduced until a spatial location on the border 406 of the color Doppler image 400 is in the same location as a spatial location of the border 404 of the region of interest 131. By automatically reducing the size of the color Doppler image 400, the frame rate of the color Doppler image 400 is increased. Increased frame rate provides better resolution.

The automatic region of interest adjustments discussed above can be used for any combination of ultrasound parameters. For example, display 400 may be a B-mode intensity display. Further, the ultrasound system 400 shown in FIG. 15 also automatically adjusts the color Doppler image 400, or any other image 130, as discussed above. In particular, the microprocessor 420 controls beamformer 402 and transducer 430 to obtain echo signals and move the color Doppler image 400. Alternatively, the microprocessor 127 (FIG. 1), 420 may not allow a region of interest 131 to be designated outside of the color Doppler image 400.

In addition to controlling movement of the color Doppler image 400, the microprocessor 127 alters the image plane data. Referring to FIGS. 1 and 2, the ultrasound system 100 allows operator designation of velocity direction angles within a region of interest 131 for velocity angle correction. Using the user interface 133 in combination with the microprocessor 127, the operator places an icon 270 within the region of interest 131. A line passing through icon 270 displays an angle. Further, a numeric display of the angle is also placed on the image 130. The line is positioned parallel to the flow of fluid in the region of interest 131 by the operator. The angle of the line passing through the icon 270 is incremented by the operator using user interface 133, a paddle switch or rotating knob in particular. Preferably, the angle is incremented in one degree increments either clockwise or counter-clockwise, depending on the paddle switch or rotating knob operation. The microprocessor 127 then assigns the angle associated with icon 270 as the velocity direction angle for each spatial location within the region of interest 131.

For multiple regions of interest 131, a velocity direction angle is determined for each region of interest 131. Furthermore, the microprocessor 127 may automatically place the icon 270 in the center of a selected region of interest 131 for convenience of the operator.

Multiple designations of the velocity direction angle within a particular region of interest 131 are possible. The operator controls user interface 133 to place multiple icons 270 in the particular region of interest 131. Velocity direction angles are selected for each of the icons 270.

Application of the multiple velocity direction angles to spatial locations within the region of interest 131 is performed by several alternative methods. One method generates an interpolated angle for spatial locations between two icons 270, as for example by linear interpolation. For other spatial locations within the region of interest, the angle is extrapolated based on the angles associated with the nearest icons 270.

A second method uses a nearest neighbor technique. For all spatial locations in the region of interest 131, the microprocessor 127 assigns the angle associated with the nearest icon 270 as the velocity direction angle.

Once the velocity direction angle for each spatial location in the region of interest 131 is assigned, microprocessor 127 obtains Doppler velocity image plane data from buffer 123. The microprocessor 127 then corrects the Doppler velocity image plane data in accordance with a velocity correction angle. The velocity correction angle at any point in the region of interest 131 is the difference between the Doppler line angle and the velocity direction angle at that point. At each point $(X_i, Y_i)$ in the region of interest 131, the Doppler line angle in the display raster XY coordinate space is given by $\arctan((X_i-X_{apex})/(Y_i-Y_{apex}))$ where $(X_{apex}, Y_{apex})$ are the display coordinates of the apex of the scan format. The velocity value for each location is then divided by the cosine of the velocity correction angle.

The velocity values from the Doppler velocity image plane data are also corrected in accordance with a line dependent direction angle. Where the ultrasound scan lines are in the linear or steered linear format, the ultrasound lines are all parallel and at a constant angle to the region of interest 131, and no line dependent correction is made. However, in the sector, VECTOR® and curved linear array formats, angle correction is further dependent on the Doppler line angle. The angle correction is adjusted as function of the difference of each scan line angle from the user entered velocity direction angle.

The angle corrected Doppler velocity image plane data is used for various calculations and displays. For example, the angle corrected Doppler velocity image plane data is displayed as an angle corrected flow profile for a cross section. By angle correcting the Doppler velocity values, the velocity image plane data more accurately represents the velocities in the region of interest 131.

Referring to FIG. 15, the microprocessor 420 also corrects the Doppler velocity image plane data as discussed above. Doppler velocity image plane data from both buffers 412 and 414 is corrected.

Other alterations of the image plane data are desirable, such as conversion to a linear scale. Due to log compression of the echo signals, the image plane data is in the log scale.

The conversion from log scale to linear scale is complicated by quantization effects due to the spacing of the higher linear values. The microprocessor 127 applies an algorithm to reduce any quantization effects. The echo signal may also be preconditioned to remove quantization effects.

Image plane data for each point in a particular region of interest 131 is converted by applying a reverse log compression and scaling algorithm ("reverse log compression"). The microprocessor 127 applies the algorithm to the image plane data. For reverse scaling, the image plane data value for each point is applied to a look-up table to determine a reversed scaled value. The reverse scaled value is then compared to look-up table values to determine a reversed compressed value. The reversed compressed value is in the linear scale. The linear values are used to perform various calculations.

For example, a linear average B-mode intensity is calculated for the region of interest 131. Each B-mode intensity value is obtained from buffer 123. The microprocessor 127 reverse log compresses each value. The linear B-mode intensity values are added to obtain a total linear B-mode intensity for the region of interest 131. The total linear B-mode intensity is divided by the number of points in the region of interest 131 to obtain the linear average B-mode intensity. Further, the linear average B-mode intensity calculation is limited to B-mode intensities within a selected range of values. In this limited range calculation, the number of points corresponds to the number of points associated with B-mode intensities in the selected range.

Referring to FIG. 15, the microprocessor 420, using the look-up table 446, passes linear values to the accumulator 444. As discussed below, the accumulator 444 sums values for use in various calculations. Thus, the ultrasound system 400 is also capable of converting the image plane data to a linear scale.

Referring to the embodiment shown in FIG. 1, an alternative method to convert data to a linear scale is provided. Instead of converting each value to a linear scale, a histogram format is used. The microfiche appendix contains code for applying the histogram format. Generally, the coordinates 1X, 1Y, 2X and 2Y are provided. The code uses the coordinates to define an area. Image plane data within the area is obtained and a histogram is created. This method, as represented in FIG. 3, increases the speed of calculating higher order statistics.

As represented by block 127b, a histogram format is applied by the microprocessor 127. The microprocessor 127 obtains the image plane data from buffer 123. The microprocessor 127 uses the histogram format to calculate a quantity as represented by block 127c. Referring to FIG. 4, the histogram format is symbolized graphically as histogram 200. Preferably, the histogram 200 has two hundred and fifty six (256) bin ultrasound values corresponding with 256 bins 201. Histograms 200 of other sizes could be used.

Figure 3:
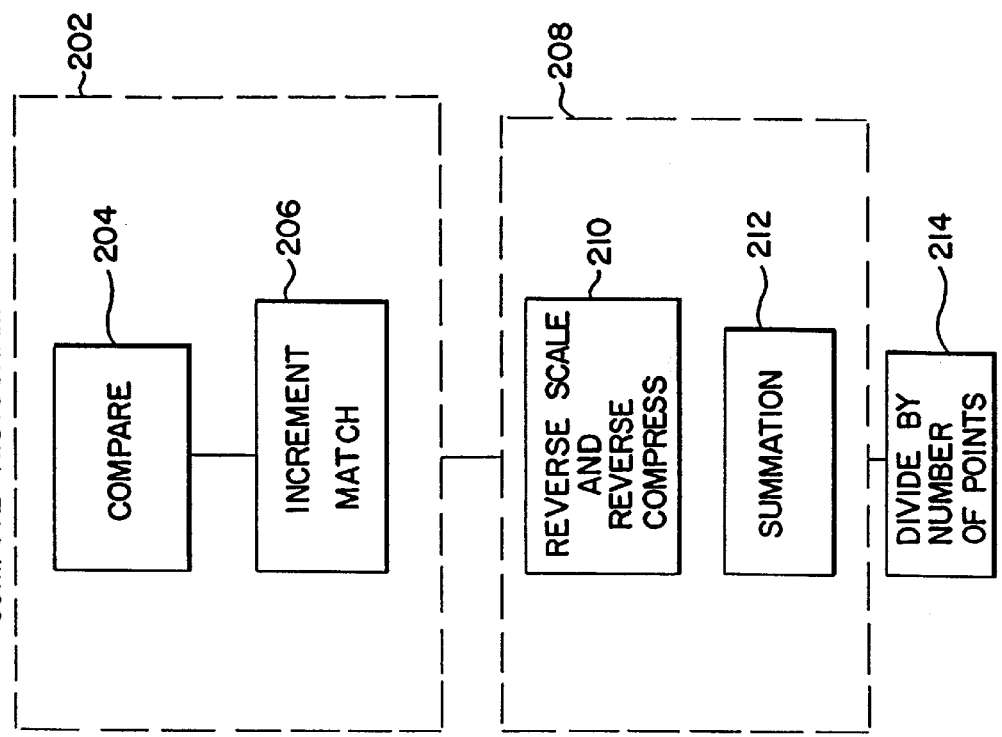
FIG. 3 is a block flow diagram for performing linear calculations using a histogram.

Referring to FIGS. 3 and 4, to convert the image plane data to the linear scale, the histogram 200 is computed as represented by block 202. As an example, B-mode intensity may be selected as the ultrasound parameter of interest within a selected region of interest 131. Other ultrasound parameters may be used. In this example, the B-mode intensity for each point within the region of interest 131 is compared to bin B-mode intensity values of the histogram 200 as shown by block 204. For each B-mode intensity equal to or within the range of one of the histogram's bin B-mode intensity values, the bin 201 corresponding to the bin B-mode intensity value is incremented by one as shown by block 206. Thus, the histogram 200 is computed with a weight assigned to each bin of the histogram. The total weight associated with each of the bins 201 comprises bin data.

The bin B-mode intensity value for each of the bins 201 is converted in block 208 to the linear scale. For each of the bin B-mode intensity values, a reverse log compression algorithm is applied as shown by block 210. Preferably, a look-up table contains the reverse log compressed values for each of the known bin B-mode intensity values.

Referring to FIG. 1, the reverse log compression function is based on the operator's log compression adjustment of image 130, as discussed above with respect to FIG. 12B. The microprocessor 127 obtains the log compression setting and generates the look-up table based on the log compression setting. The look-up table provides a linear value for each bin value in the log scale. FIG. 6C demonstrates one possible function for reverse log compression. Referring back to FIGS. 3 and 4, a linear bin ultrasound value is obtained for each of the 256 bins 201 in block 210. Any subsequent calculations based on the bin ultrasound values and the bin data are in the linear scale.

Figure 5:
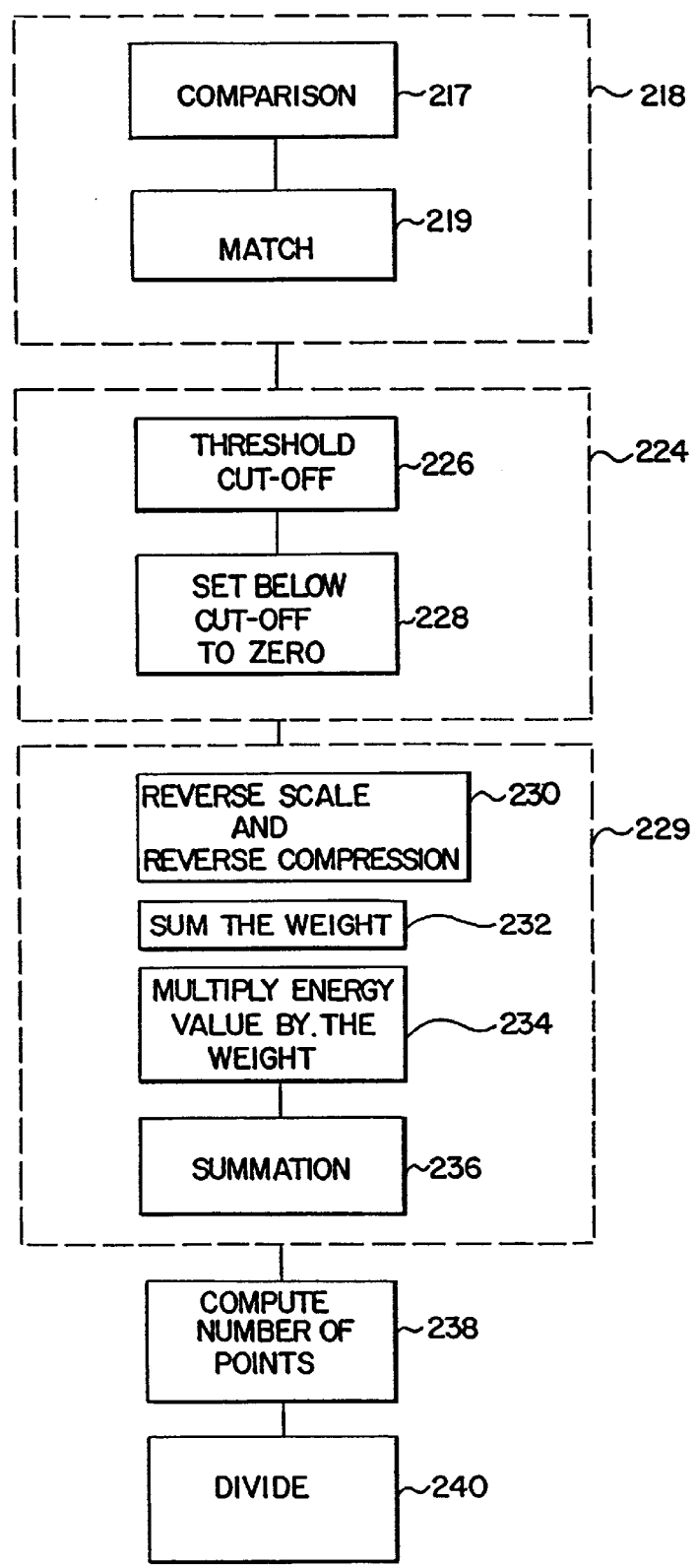
FIG. 5 is a flow diagram for performing linear calculations using a two-dimensional histogram.

As an alternative to applying the one-dimensional histogram 200, in some applications a two-dimensional histogram 216 is applied to convert data to the linear scale. Referring to FIGS. 1, 4B and 5, the microprocessor 127 creates two-dimensional histograms 216. Creation of the histogram is demonstrated by block 218 in FIG. 5. The two-dimensional histogram 216 shown in FIG. 4B comprises velocity and energy dimensions. Other information or ultrasound parameters can be used.

The histogram 216 includes 64 velocity bins or columns along the velocity axis and 64 energy bins or rows along the energy axis. Each velocity bin has a bin velocity value while each energy bin has a bin energy value. The intersection of an energy bin with a velocity bin represents a particular bin velocity value and energy value. Other sized two-dimensional histograms 216 may be used.

The microprocessor 127 obtains the energy value and velocity value from the image plane data in buffer 123 for each spatial location in the region of interest. The energy and velocity values are compared to the bin energy and velocity values, respectively, of the two dimensional histogram 216 in block 217 until a match is found. The weight (w) of the intersection of the matched bin velocity value with the matched bin energy value is increased by one (1) in block 219. After all the energy and velocity values associated with each spatial location are matched, the two-dimensional histogram 216 is complete.

For use in the microprocessor 127 based system of the preferred embodiment, the two-dimensional histogram 216 is treated as a series of one-dimensional histograms 200. For the example above and as shown in FIG. 4C, each histogram 200 of velocity bins (0–63) represents a particular energy bin as shown in FIG. 4C. Thus, sixty four (0–63) energy histograms 200 are provided.

Once the two-dimensional histogram 216 is created, microprocessor 127 converts the bin ultrasound values to the linear scale. Alternatively, the set ultrasound values remain in the log scale for calculations in the log scale.

Three dimensional histograms are also created. Thus, yet another ultrasound parameter or time is used in creating the histogram. Any bin ultrasound values associated with the third dimension are also converted to the linear scale for linear calculations.

The histogram format is also useful for altering the image plane data by applying a threshold or baseline shift. For the embodiment shown in FIG. 15, the application of a baseline shift and any threshold is controlled by microprocessor 420 without creating the histogram, as discussed below.

Referring to FIGS. 1 and 4, the baseline shift discussion below demonstrates application of the baseline shift to the one-dimensional histogram 200. Application to the two-dimensional histogram 216 is comparable.

Baseline shift, as known in the art, accounts for obviously erroneous values in the velocity image plane data in buffer 123. Erroneous velocity values from the velocity image plane data in buffer 123 are reassigned the appropriate value by microprocessor 127.

For applying a baseline shift, the histogram 200 is created from Doppler velocity values from the image plane data. Using the histogram 200, the baseline shift is performed on the bin velocity values. Referring to FIG. 14A, a region of interest 131 is selected across a vessel. FIG. 14B demonstrates the actual velocity values obtained before baseline shift as a function of distance for the region of interest 131.

FIG. 14C graphically demonstrates the histogram 200 created from the actual velocity values. For this example, the negative bin velocity values are erroneous. The negative bin velocity values represent velocity values above positive Vmax and are reassigned to histogram bin velocity values greater than positive Vmax.

More particularly, the histogram 200, assuming sixty four (64) velocity bins, has positive velocity values assigned to bins zero (0) through thirty one (31). Bin thirty two (32) is assigned the largest negative value with incrementally smaller negative values assigned through bin sixty three (63). Exceeding the bin value associated with bin thirty one (31) represents exceeding the Nyquist velocity. For this example, all bin values associated with negative velocity are shifted to associate with positive velocities. Thus, bin values for bins thirty two (32) through sixty three (63) are baseline shifted. Alternatively, the baseline shift operation occurs as the histogram is created.

In the example above, the microprocessor 127 baseline shifted all negative bin velocity values, or bins 201 associated with a one (1) $V_{max}$ range. More or less baseline shifting of the two (2) $V_{max}$ range, resulting in more or fewer positive values, may be used. The baseline may be shifted by fractions of the number of bins 201 in the histogram 200. Generally, positive verses negative values demonstrate flow towards or away from the transducer 104.

FIG. 14D represents baseline shifting the histogram 200 of FIG. 14C by ⅔ of $V_{max}$. Bins 201 numbered 32 through 54 are baseline shifted. FIG. 14E demonstrates a velocity profile curve created from the histogram 200 of FIG. 14D. The baseline shifted linear velocity surface integral waveform, or profile, is displayed within the region of interest in FIG. 14A.

The histogram 200 also provides a convenient method for applying a threshold to the image plane data. As known in the art, the operator can adjust the user interface 133 to select a threshold to be applied to the image plane data, such as for rejecting lower velocities. Referring to FIGS. 1 and 4, the microprocessor 127 applies the threshold to the histogram 200, two dimensional histogram 216 or a three dimensional histogram. Applying the threshold removes the weight associated with particular values in the image plane data. For example, applying a threshold to the two dimensional histogram 216 is discussed below.

The microprocessor 127 applies the threshold to the bin ultrasound values of any of the ultrasound parameters, such as color Doppler energy, velocity or variance or B-mode intensity. In the two-dimensional histogram 216, the threshold is applied to the bin ultrasound values associated with one parameter prior to calculations based on image plane data associated with either parameter of the histogram.

A threshold process is shown in FIG. 5. As discussed above with respect to creation of the two dimensional histogram, the two dimensional histogram 216 corresponding to energy and velocity values is created in block 218. Other ultrasound parameters or time could be used.

To apply the threshold as shown by block 224, the threshold cut-off value is obtained in block 226 from the user interface 133 via the microprocessor 127. For velocity, the threshold cut-off value is applied to positive and negative bin velocity values. As shown by block 228, the bin data corresponding to intersections of bin energy values with a positive or negative bin velocity value below or above the positive or negative cut-off value, respectively, are set to zero. For example and in reference to FIG. 4C, the velocity bins below the cut-off in each energy histogram are set to zero. As a further example and assuming a cut-off value of two, the bin data associated with the cross hatched area in FIG. 4B is set to zero. Thus, the two-dimensional histogram 216 contains bin data above zero corresponding to spatial locations above the velocity threshold. The threshold may also be applied to remove high values, a range of values or high and low values.

Many possible combinations can be used to threshold various parameters based on other various parameters to more accurately reflect what the user sees on the ultrasound image 130 or to obtain various measurements. One example is discussed below with respect to automatic area detection.

Turning to FIG. 10, a region of interest 131 includes portions of a blood vessel 300. The microprocessor 127 obtains image plane data (such as Doppler velocity values) for each spatial location within the region of interest 131. A threshold cut-off is then selected. In the velocity example above, the threshold cut-off defines a velocity value separating velocity values corresponding to tissue motion from velocity values corresponding to fluid or blood motion. The threshold cut-off may vary, as previously discussed, due to operator input and the structure represented within the region of interest 131. Based on the threshold cut-off and the velocity values for each point in the region of interest 131, the microprocessor 127 determines a microprocessor region of interest 302. The microprocessor region of interest 302 corresponds to spatial locations within the region of interest 131 with corresponding velocity values above the cut-off.

As another example, a threshold cut-off is applied to B-mode intensity values. The echo signals used to derive the B-mode intensity values are obtained and passed through a spatial or temporal low pass filter to smooth the echo signals for reliability. The threshold cut-off is then applied to the corresponding B-mode intensity values from the image plane data. Preferably, the threshold cut-off is selected to define B-mode intensities associated with structure from B-mode intensities not associated with structure. The pixels corresponding to structure surrounding pixels corresponding with no structure define the area of the microprocessor region of interest 302. The microprocessor region of interest 302 may not be a set of contiguous points. For example, a blockage or other tissue may exist within or protruding into a vessel and not be included in the microprocessor region of interest 302. Once the microprocessor region of interest 302 is determined, the microprocessor region of interest 302 is highlighted on the image 130.

For structure that changes position or size over time, such as the heart, the microprocessor 127 creates multiple microprocessor region of interests 302 as a function of time. The same operator region of interest 131 is used for creating each microprocessor region of interest 302. The heart walls change in size and shape over time, based on the heart cycle. The microprocessor 127 automatically accounts for the changes by creating the microprocessor region of interest 302 on a per frame or multiple frame basis over a portion of a heart cycle, a single heart cycle or multiple heart cycles.

Referring to FIGS. 1 and 10, the region of interest 131 or microprocessor region of interest 302 are used for various calculations. The microprocessor 127, as demonstrated by block 127c, calculates any desired quantities based on the corrected and/or converted image plane data in buffer 123. The calculations are based on displayed image plane data or non-displayed image plane data. Alternatively, the calculations are based on acoustic ultrasound signal values or color value based ultrasound signal values. The quantities are derived using the histogram 200, two-dimensional histogram 216 or three dimensional histogram.

Using different parameter values, such as Doppler energies or B-mode intensities, for the calculations provides different measurements indicative of conditions in the body. For example, the surface area of Doppler energy for a given time is calculated to provide a measure of blood perfusion.

Referring to FIGS. 3 and 4, use of the histogram 200 to calculate a quantity is shown. For example, a linear average B-mode intensity is calculated. The histogram 200 derived from B-mode intensities and converted to the linear scale is obtained as discussed above. Each linear bin B-mode intensity value is multiplied by the histogram weight associated with the bin B-mode intensity value. The resulting weighted linear bin B-mode values are then summed for each bin 201 in block 212. The sum represents a total linear B-mode intensity for the region of interest 131.

The average linear B-mode intensity is calculated by dividing the total linear B-mode intensity by the number of points in the region of interest 131, the sum of the bin data. The average linear B-mode intensity can be log scaled and compressed so that the value conforms to the units (dB) of the image 130. Furthermore, the bin ultrasound values can be left in the log scale to obtain an average log B-mode intensity.

Other higher order quantities are conveniently calculated using the bin data of histogram 200. A waveform or curve of the bin data of histogram 200 is created as a function of the bin ultrasound values. The waveform represents the weight or number of occurrences of a particular value as a function of the various bin ultrasound values. Various quantities are derived from the waveform. For example, the standard deviation of the waveform is calculated. As another example, the linear standard deviation is readily available from the histogram 200 after converting the bin ultrasound values to the linear scale.

A waveform of the bin data of histogram 200 as a function of bin ultrasound values in the log scale is also created by microprocessor 127. From the waveform of the histogram 200 in the log scale, a log weighted average or log weighted standard deviation is calculated. Using appropriate reverse log compression and the bin data of histogram 200, a variety of quantitative values and waveforms are calculated.

The microprocessor 127 also calculates quantities using the bin data and bin ultrasound values of the two-dimensional histogram 216. For the example and as demonstrated by FIG. 5, an average energy for fluid in a linear scale is calculated using the bin data from the two-dimensional histogram 216. Other quantities, calculated as a function of energy values or values associated with other ultrasound parameters may be used.

As discussed above with respect to FIG. 5, the two-dimensional histogram 216 is derived from energy and velocity values. Also as discussed above, the threshold cut-off is applied to the two-dimensional histogram 216 to set the bin data associated with low velocity values to zero.

A total energy in the linear scale is then calculated as shown in block 229. As discussed above, the bin energy values are converted to the linear scale in block 230. The weight corresponding to each bin energy value is then obtained in block 232. The weights from each intersection of each particular bin energy value with the various bin velocity values are added. For velocities below the threshold, the weight is set to zero, so the low velocity energies are not added to the weight of each bin energy value. The linear bin energy values are multiplied by the weight corresponding to each bin energy value as shown in block 234. Finally, the weighted linear bin energy values for each bin 201 or bin energy value are summed in block 236 to obtain a total linear energy or surface integral of Doppler energy.

To determine the average linear Doppler energy, the number of points corresponding to velocities greater than the threshold are calculated in block 238. All the weighting values, or bin data, in the two-dimensional histogram 216 are summed by microprocessor 127. Since the weights associated with low bin velocity values are set to zero, the spatial locations associated with the low velocity values are not included in the summation. The summation represents the total number of spatial locations with a velocity value above the threshold.

Finally, in block 240, the total linear Doppler energy is divided by the total number of spatial locations with a velocity value above the threshold. The result is the average linear Doppler energy or the normalized surface integral of Doppler energy. Further, since low velocity points are removed by applying the threshold, energy signals associated with slow moving tissue are removed. Only energy values from the image plane data associated with the more rapidly moving fluids are included in the calculation. To calculate average linear Doppler energy for all energies in the region of interest 131, the velocity threshold cut-off is not applied.

Other calculations are made using the two-dimensional histogram 216. Referring to FIG. 4 and for example, the two-dimensional histogram 216 where one dimension corresponds to time and the second dimension corresponds to an ultrasound parameter, such as Doppler energy, is created. The two-dimensional histogram 216 is used to create a time averaged histogram 200.

The histogram 200 of the average weight over time as a function of the bin energy values is created by the microprocessor 127. The weights from the intersection of all the time bins with each bin energy value of the two-dimensional histogram 216 are summed. The summed weights are then divided by the number of time bins to obtain an average weight as a function of time for each energy bin. The result is histogram 200 with bin data corresponding to the average occurrence of the bin energy values as a function of time.

The histogram 200 of Doppler energy averaged as a function of time is used to calculate various quantities, such as a surface integral of Doppler energy averaged as a function of time. Other histograms 200 may be created representing a weighting of one ultrasound parameter distributed across the bin values for another ultrasound parameter or time.

The histogram format is used to calculate quantities associated with the microprocessor region of interest 302. Using microprocessor region of interest 302, quantities are calculated without applying a threshold to the image plane data used for the calculation. For the embodiment shown in FIG. 1, a two-dimensional histogram of low pass filtered B-mode intensities and B-mode intensities is created. Low pass filtering the B-mode intensities spatially averages the intensities as known in the art. As discussed above, a threshold is applied to the low pass filtered B-mode intensities to determine the microprocessor region of interest 302. The remaining B-mode intensities are then used to perform various calculations, such as the integration of B-mode intensity over an area. The quantities include B-mode intensities above and below the low-pass filtered B-mode threshold value. Other parameters, such as energy, can be used.

Various calculations and displays are also based on each microprocessor region of interest 302 over time. For example, the microprocessor region of interest 302 and an average Doppler energy value for the microprocessor region of interest 302 for each of multiple frames of image plane data is determined.

Referring to FIG. 15, the same calculations as discussed above are performed without applying the histogram format. Instead, a look-up table and accumulator structure is provided for determining various quantities.

In particular, the output of multiplexer 432 includes the image plane data and/or region Id. Alternatively, acoustic or color value based ultrasound signal values are used. The image plane data is applied along signal path 436 to a parameter selector 442, and the region Id information is applied to calculation area accumulators 444. The parameter selector 442, in response to the microprocessor 420, selects the appropriate data from the image plane data, such as data corresponding to Doppler energy values. The appropriate data is supplied to the lookup table 446. Lookup table 446 maps such data onto values that are supplied to accumulators 444. Some of the output values are in the linear or log scales as discussed above. Instead of lookup tables 446, other mapping devices such as threshold or scaling devices may also be used. The threshold cut-off value is selected as a high, low or range to remove various values. The accumulators 444 output quantities summed from the input values.

Figure 16:
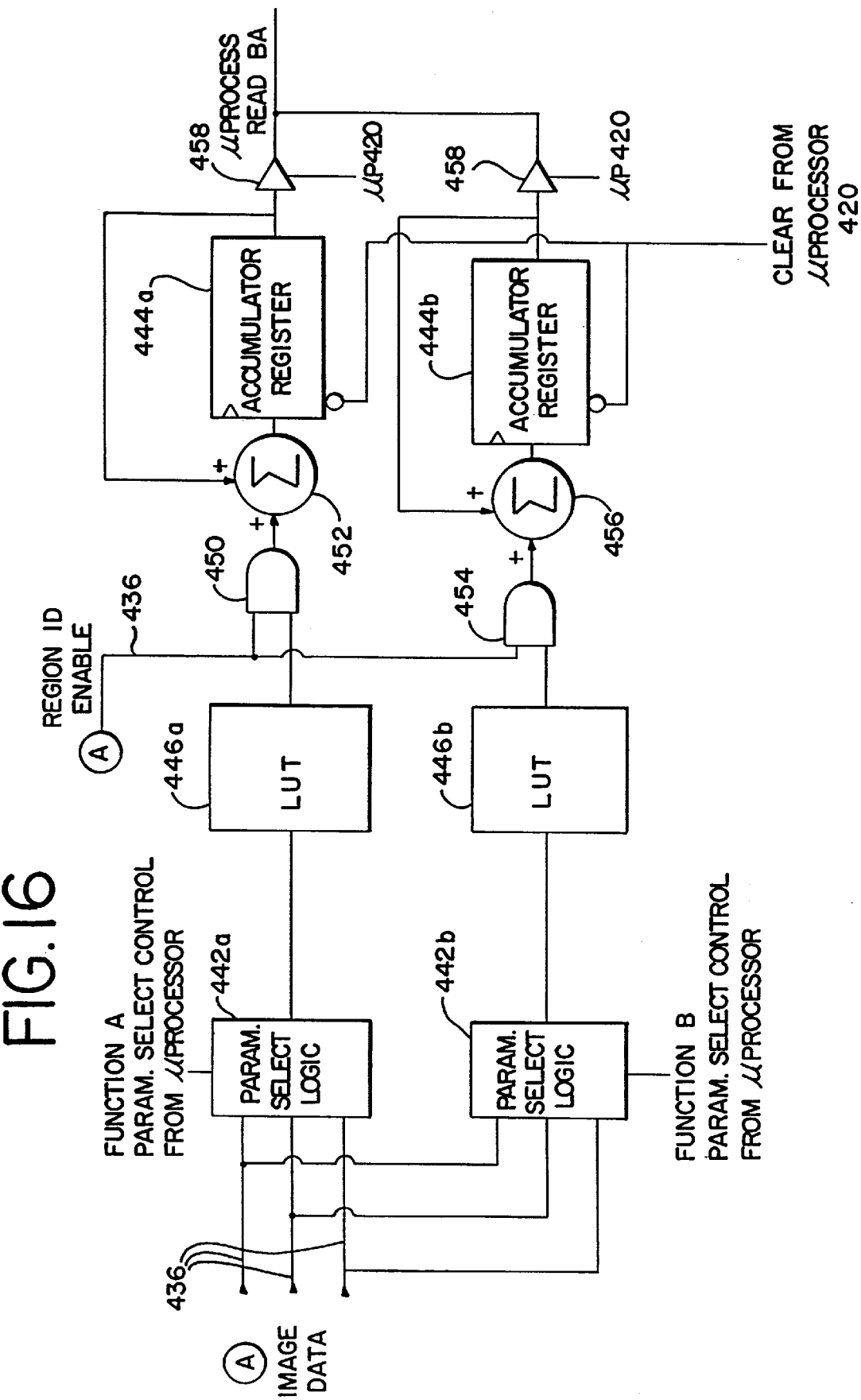
FIG. 16 is a circuit diagram illustrating in more detail a portion of the circuit of FIG. 15B.

FIG. 16 is a schematic circuit diagram illustrating in more detail the functions and construction of the parameter selector 442, accumulators 444 and the lookup table 446. As shown in FIG. 16, the parameter selector 442 includes two parameter select logic circuits 442*a*, 442*b* for selecting the appropriate B-mode and Doppler image plane data.

The bits selected by the parameter select logic circuit 442*a* are supplied to the lookup table 446*a*. The lookup table 446*a* applies a threshold to the selected bits to determine whether there is valid fluid flow data associated with the particular pixel. If there is valid fluid flow, the lookup table 446*a* outputs a 1 to AND-gate 450. Otherwise, the lookup table 446*a* supplies a 0 to the AND-gate 450. The enable bit of line 436 is also supplied to the AND-gate 450. If the particular pixel data processed is not within the region of interest 131, the enable bit of line 456 is set to 0, thereby forcing the gate output to 0 so that such pixel is not counted in the accumulator 444*a*; otherwise a 1 is supplied to gate 450.

If AND-gate 450 supplies a 1 to an adder 452, the adder 452 adds 1 to the value stored in the accumulator register 444*a* and applies this updated value to replace the one stored in the accumulator register 444*a*. In this manner, the B-mode and/or Doppler image plane data is used to determine whether the pixel is counted as part of the region of interest 131 associated with fluid flow. For example, if the B-mode intensity is high, the corresponding Doppler values may not be a reliable indication of fluid flow. In this case, the lookup table 446*a* outputs a 0 rather than a 1. In some applications, the Doppler data above, such as Doppler velocity data, may be adequate for determining the validity of the data. The same considerations also apply to qualifying the validity of the image plane data processed in the parallel path described below.

In parallel, the parameter select logic 442*b* selects the appropriate bits, such as Doppler energy or B-mode values, from the image plane data from multiplexer 432. The selected bits are supplied to the lookup table 446*b*. In a manner similar to that described above for lookup table 446*a*, lookup table 446*b* applies a selection criteria to output the selected bits if the data is qualified, such as through application of a threshold, and a 0 if the data is not qualified as valid. The output is supplied to AND-gate 454. AND-gate 454 is a multi-bit gate. AND-gate 454 is also controlled by the region Id enable bit in a manner similar to AND-gate 450. Adder 456 then adds the output of AND-gate 454 to the stored value in accumulation register 444*b* and supplies the updated value to replace the stored value in accumulator register 444*b*.

The buffers 412 and 414 each store an entire frame of image plane data. After an entire frame of information is processed through the two signal paths in FIG. 16, accumulator 444*a* contains a count indicating the number of qualified pixels where there is significant fluid flow in the region of interest. Accumulator register 444*b* contains a summed value of a parameter, such as velocity. The values stored in the two accumulator registers 444*a*, 444*b* are then read by the microprocessor 420 through two tri-state buffers 458 controlled by the microprocessor 420 and stored in the microprocessor memory. The above-described process for counting the number of qualified pixels and integrating qualified parameter values is performed for each of multiple frames.

The microprocessor 420 performs calculations using the accumulated information. By multiplying the number of pixels by the area per pixel, an area measurement is obtained for the region of interest 131 for each of the multiple frames. By dividing the sum of qualified parameter values by the number of qualified pixels, an average parameter for each of the several frames is obtained. Other calculations may be performed using this information.

Figure 17:
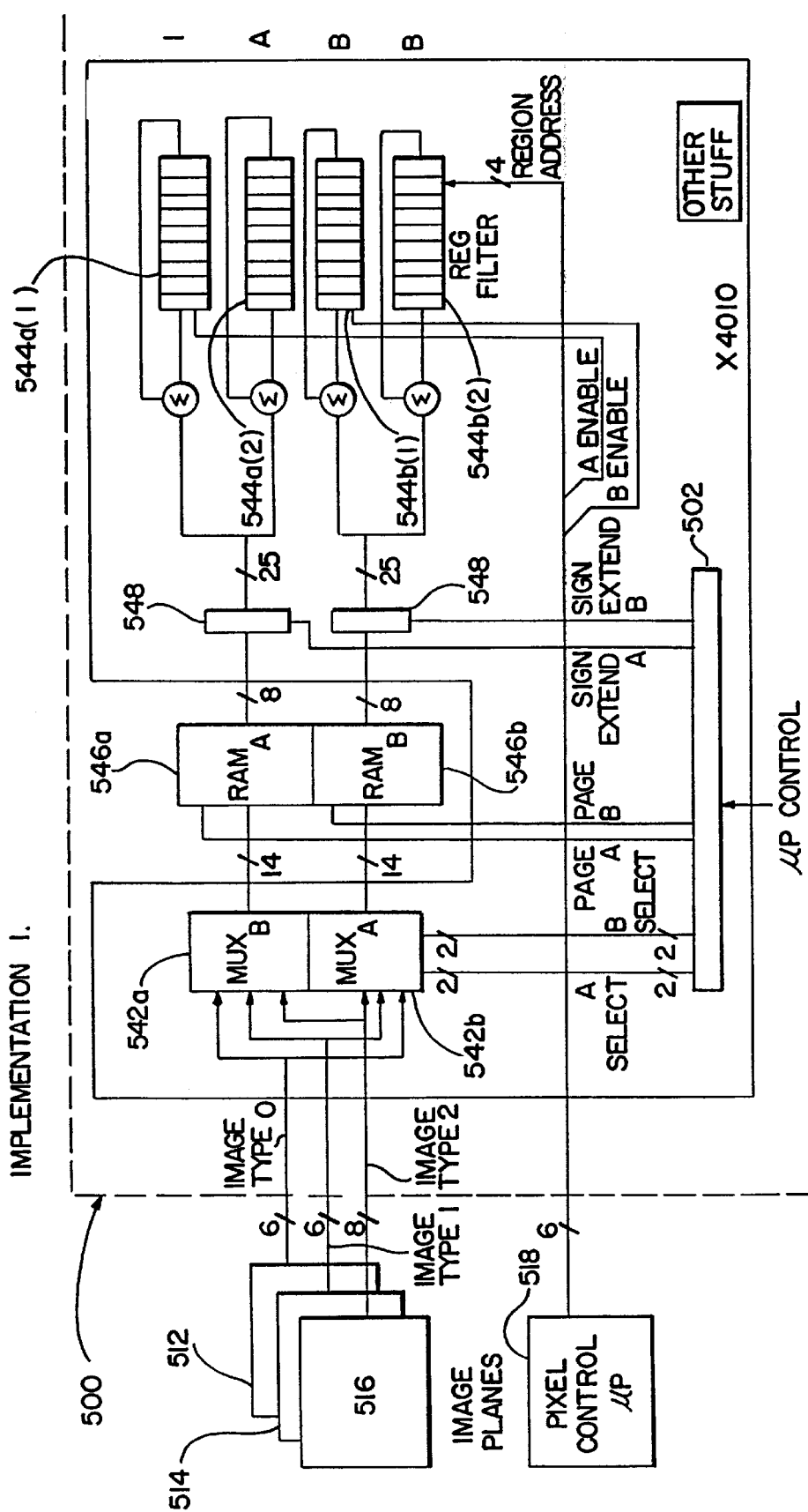
FIG. 17 is a block diagram illustrating in more detail one implementation of the circuit of FIG. 16.

One implementation of the embodiment of FIG. 16 is illustrated in more detail in the block diagram of FIG. 17. The embodiment shown in FIG. 17 includes circuit functions equivalent to the image planes shown in FIG. 15A and the circuit 500 which performs all the functions of FIG. 16. The circuit 500 receives Doppler and B-mode image plane data from three buffers 512, 514 and 516. Buffers 512, 514 and 516 correspond respectively to the Image Type 0, Image Type 1 and Image Type 2 planes of data in buffers 412, 414 of FIG. 15A. The image plane data from the buffers 512, 514 and 516 is supplied in parallel to two multiplexers 542*a* and 542*b*. Multiplexers 542*a* and 542*b* are controlled by register 502 using two select lines, A select and B select. Each of the two multiplexers 542*a* and 542*b* selects the appropriate bits of information from buffers 512, 514 and 516 and supplies the bits to a corresponding lookup table 546a or 546b. Lookup tables 546a and 546b comprise random access memory devices. The lookup tables 546a and 546b are controlled by register 502 using page selects PAGEA and PAGEB.

The circuit 500 includes two pairs of accumulators: a first pair 544a(1), 544a(2) and a second pair 544b(1), 544b(2). In each pair of accumulators, one accumulator 544a(1) and 544b(1) accumulates or integrates image plane data associated with even-numbered pixels and the other accumulator 544a(2) and 544b(2) accumulates or integrates image plane data associated with odd-numbered pixels. The accumulators within each of the first pair 544a(1) and 544a(2) and the second pair 544b(1) and 544b(2) are arranged in parallel to increase the speed of the accumulation process.

The lookup tables 546a and 546b map the received bits onto selected stored values and supply outputs to two sign extension controls 548. Each of the sign extension controls 548 supplies sign extended signals to one of the first pair 544a(1) and 544a(2) or the second pair 544b(1) and 544b(2) of accumulators. Each of the four accumulators has sixteen registers addressed by a four bit region address signal from pixel control map 518. Pixel control map 518 performs a function similar to that of the region Id section of the image planes of FIG. 15A. In this manner, each of the four accumulators is capable of accumulating up to sixteen different calculation areas. The calculation areas correspond to multiple regions of interest 131 (FIG. 2).

Pixel control map 518 provides control bits for A enable and B enable. The control bits control accumulation of a single quantity, such as area or velocity, without accumulating the values of a second quantity.

Figure 18:
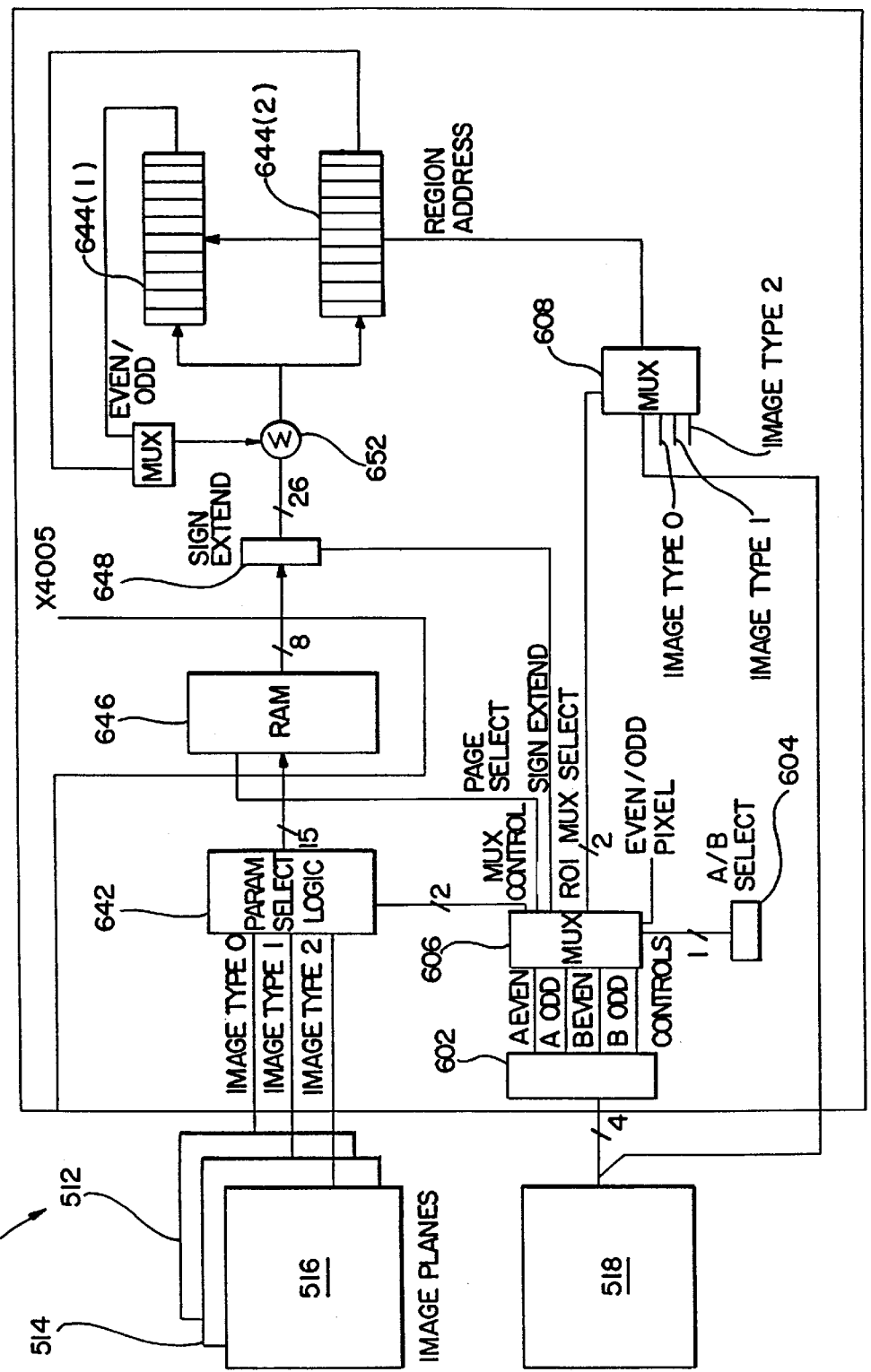
FIG. 18 illustrates another implementation of the circuit of FIG. 16.

FIG. 18 illustrates an alternative embodiment to that of FIG. 17 for accumulating quantities. As shown in FIG. 18, system 600 has essentially the same overall structure as shown in FIG. 17 except that the number of multiplexers (e.g. 642), lookup tables (e.g. 646) and accumulators (e.g. 644(1), 644(2)) are reduced. Additional control circuits, such as control register file 602, A/B select register 604, and multiplexers 606, 608, are provided to control parameter multiplexer 642, lookup table 646, sign extension control 648, and accumulators 644 (1), 644 (2). The additional control circuits control selection of particular image plane data corresponding to the particular region of interest 131 (FIG. 2) and the desired quantity.

Figure 19:
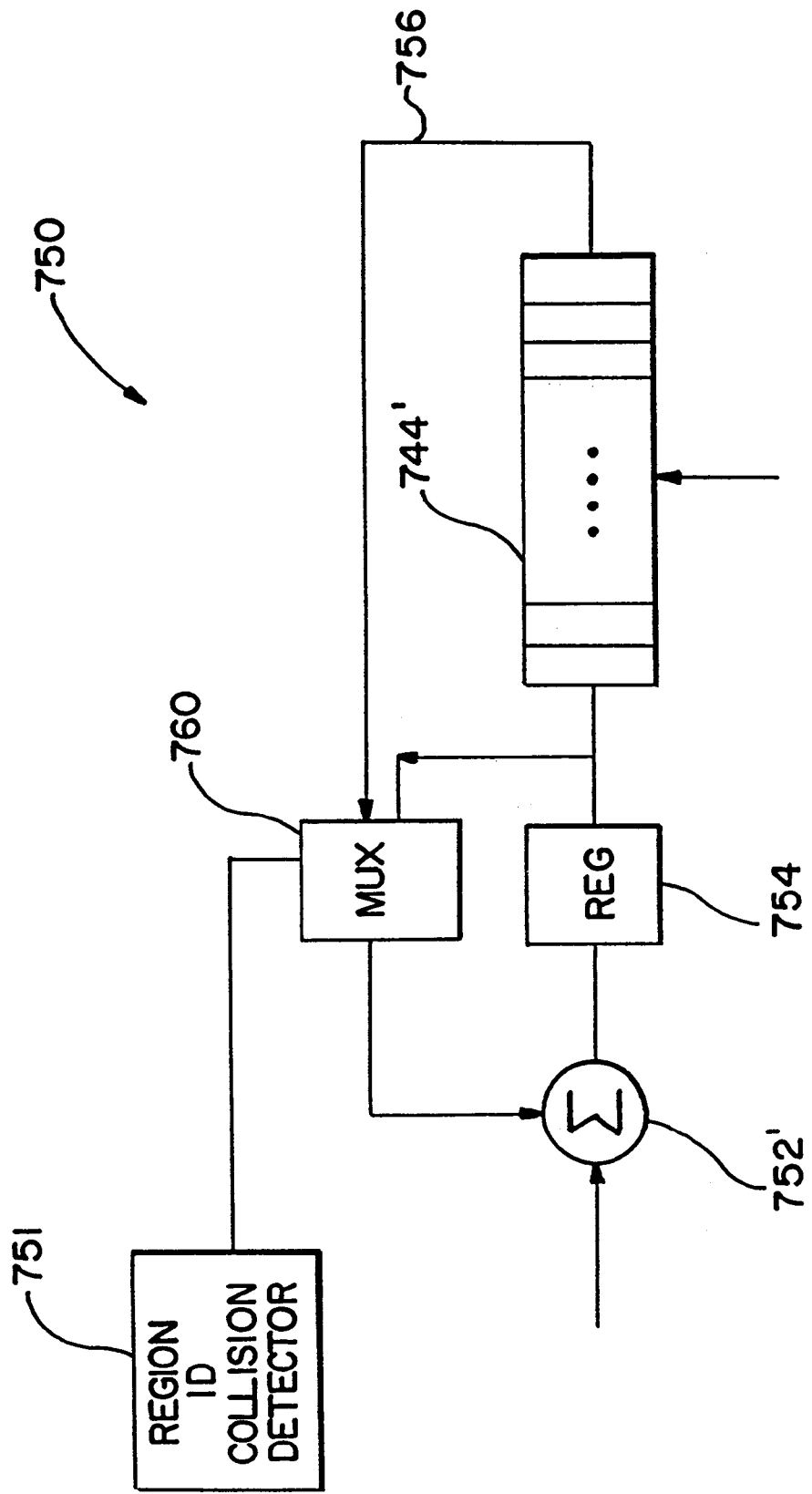
FIG. 19 is a schematic circuit diagram illustrating a circuit useful for implementing the circuit of FIG. 18.

Referring to FIG. 19, a schematic circuit diagram illustrating a circuit 750 useful for the device shown in FIG. 18 is shown. The accumulators 644(1) and (2) are replaced with the circuit 750. Obtaining a value from each of the two accumulators 644(1), 644(2) takes considerable time. When the value is sent to adder 652, as shown in FIG. 18, the value may already be stale. The circuit shown in of FIG. 19 compensates for stale values from accumulators 644(1) and 644(2) by using the circuit 750. A region Id collision detector 751 compares the region Id that is associated with the value at the input to the accumulator with the region Id associated with the value being written to memory 744'. Based on the comparison, the region Id collision detector 751 selects which of the multiplexer 760 inputs to be applied to adder 752'.

For either of the alternative embodiments shown in FIGS. 17, 18 and 19, quantities are calculated using accumulators. Calculating the quantities occurs immediately after real-time acquisition of the echo signals or at a later point in time as the data is read out of the CINE 408 (FIG. 15). One quantity calculated is the cross-sectional area. Cross-sectional area is calculated by counting qualified pixels and multiplying the count by the pixel area. Other methods of integrating qualified area portions may be used and are within the scope of the invention. The cross-sectional area, or other quantities, are calculated for multiple frames of image plane data.

One possible processing sequence for acquiring frames of image plane data is:

REPEAT FOR (selected set of acquisition angles)
  FOR EACH DISPLAYED FRAME
    Processor waits for the start of vertical blank (FIG. 15A)
    Processor acquires from the hardware for the previously displayed frame
    FOR EACH REGION-ID
      read from the hardware the total number of pixels displaying
      qualified color as calculated by the hardware
      read from the hardware the sum of all qualified velocity values at pixels in a given region
  processor clears accumulators As averaged area measurements and averaged parameter values, such as velocity in this example, for each of multiple frames are computed, a temporal average is calculated based on the multiple frames of data. The temporal averaged area measurement and averaged velocity values correspond to a particular angle of measurement θ between the scan plane and the fluid flow in the vessel. The image plane data can be acquired for multiple angles of scanning, and the calculations can be derived from image plane data corresponding to the multiple angles.

As a further example of the ability of the embodiment shown in FIG. 15 to perform the same calculations as the embodiment of FIG. 1, the accumulators and look-up tables are used to obtain a quantity for the microprocessor region of interest 302. The accumulation of B-mode values is configured to depend on the low pass filtered B-mode value. If the low pass filtered B-mode value is below the threshold, then the associated spatial location is not within microprocessor region of interest 302 and the associated B-mode intensity is not accumulated. The remaining B-mode values are accumulated even if the B-mode value is above or below the low pass filtered B-mode threshold. Like the embodiment of FIG. 1, other parameters, such as energy, can be used.

Quantities are also calculated over time. Consecutive frames of image plane data spanning several Rwave cycles are obtained. A time stamp corresponding to the time of acquisition is associated with each frame of image plane data. Other times, such as the time at which various reference signals occurred (e.g., the Rwave trigger in a cardiac cycle) are also acquired and saved. ECG leads and processor 403 in FIG. 15A acquire electrocardiograms for deriving Rwave trigger signals. The time information is used to average quantities over a cardiac cycle, a portion of a cycle or multiple cycles.

An example of calculating a quantity over time corresponding to multiple angles of scanning is shown below:

Let $F(ij,k)$ represent the kth acoustic frame acquired relative to the jth Rwave trigger for the ith unique angle of scan.

The following frames of data are acquired:
$F(1,2,1), F(1,2,2), F(1,2,3), F(1,2,4), F(1,2,5), F(1,2,6), F(1,2,7), F(1,2,8)$ $F(1,3,1), F(1,3,2), F(1,3,3), P(1,3,4), F(1,3,5), F(1,3,6), F(1,3,7), F(1,3,8)$ $F(2,1,1), F(2,1,2), F(2,1,3), F(2,1,4), F(2,1,5), F(2,1,6), F(2,1,7), F(2,1,8)$

F(2,2,1),F(2,2,2),F(2,2,3),F(2,2,4),F(2,2,5),F(2,2,6),F(2,2,7),F(2,2,8)

F(2,3,1),F(2,3,2),F(2,3,3),F(2,3,4),F(2,3,5),F(2,3,6),F(2,3,7),F(2,3,8)

F(3,1,1),F(3,1,2),F(3,1,3),F(3,1,4),F(3,1,5),F(3,1,6),F(3,1,7),F(3,1,8)

The microprocessor 420 obtains sums from the accumulator registers 444a and 444b. In particular, sums over all j and k for each of the three frames 1, 2, and 3 are obtained. The sums are divided by 24 (the number frames between each Rwave trigger) to obtain an average. For example, the velocity average and pixel count average for each of the three angles scanned are obtained. A least mean square error calculation is then performed to find an area value and a velocity or other parameter value that minimizes the error for the averages acquired at the three angles. These values are then used to make various additional calculations.

One such additional calculation is the normalized surface integral of Doppler energy for the region of interest 131. The normalized surface integral of Doppler energy provides a measurement indicative of fluid conditions in the body. Either the look-up table and accumulator embodiment shown in FIG. 15, the histogram format embodiment shown in FIG. 1, or other embodiments are used to calculate the normalized surface integral or any of various other quantities.

The normalized Doppler energy for a given region of interest at any given time is represented by FIG. 6A. Other parameters, such as velocity, variance or B-mode intensity, can be used. Generally, energy values associated with low velocities are removed by applying a threshold. The function T represents applying the threshold.

The total Doppler energy in the linear scale is calculated. The total Doppler energy in the linear scale is represented by the summation from one to the number of points in the region of interest of D(Ei). D represents the reverse log compression, and Ei represents the 10 Doppler energy value at a particular spatial location (i) within the region of interest. If the histogram 200, two-dimensional histogram 216 or three dimensional histogram is used, Ei represents a weighted bin Doppler energy value. A graphical representation of D(Ei) is shown in FIG. 6C. This graph is used to develop the reverse log compression look-up table discussed above.

The total Doppler energy in the linear scale is normalized by dividing by the number of points, or spatial locations, with corresponding values above the threshold. The number of points remaining after applying the threshold is represented in FIG. 6A by the summation over all the points in the region of interest (Ti(Ei, Vi)). Thus, an average parameter is calculated. This average does not change as a function of the magnification level of acquisition and display in the ultrasound system.

The surface integral of the Doppler velocity or any other parameter may also be normalized by area. The number of points remaining is multiplied by the area of each point as part of the normalization step described above. The area represented by any given pixel is used to determine the area. Thus, a parameter density is calculated such as velocity density.

The average or other quantities, such as density, are instantaneous values. Multiple instantaneous quantities are used to derive a waveform. For example, instantaneous normalized surface integrals of Doppler energy for multiple frames of image plane data are calculated. Preferably, each surface integral is normalized by the number of points associated with energies added to the total energy. A waveform of the normalized surface integral of Doppler energy is created as a function of time. The waveform demonstrates a change in flow over time and is shown in FIG. 6B. The variation in the normalized surface integral of FIG. 6B shows a change in amount of flow over time and corresponds to changes in blood flow based on the heart cycle. Other curves as a function of other parameters may also be created.

Various quantities are derived from the normalized surface integral as a function of the heart cycle. For example, a time integral of the normalized surface integral of Doppler energy as a function of time is calculated. Referring to FIG. 1, block 127d represents the microprocessor 127 calculation of the time integral. The time integral of the normalized surface integral, as represented in FIG. 7, provides a quantity indicative of volume flow for a particular time period, Tn-1 to Tn.

Selection of the time period depends on the particular use of the ultrasound system 100 (FIG. 1) or 400 (FIG. 15). For example, the various quantities are a function of a single heart cycle, multiple heart cycles, or a portion of a heart cycle. Such calculations include the period of the heart cycle, demarcation of certain heart cycle events, ejection fraction and others.

Referring to FIGS. 1, 8 and 15 and as known in the art, ECG leads and processor 137 (FIG. 1), 403 (FIG. 15) trigger the beginning and end of the time period. Block 127e represents the microprocessor 127 use of the trigger signal from the ECG leads and processor 137 for computing further quantities. A graphical representation of the trigger signal is shown in FIG. 8B.

Instead of using ECG leads and processor 137, 403 to detect heart cycle periods, the normalized surface integral of Doppler energy is used. Other parameters may be used, such B-mode intensities. The normalized surface integral is displayed on display unit 132 or 440, as described below. The operator, using user interface 133 or 431, selects a time period for integration. In particular, icons 270 are activated and placed on the waveform. Alternatively, the user inputs the number or portion of heart cycles to integrate over. The microprocessor 127 or 420 then determines the points on the normalized surface integral waveform representing the selected time period. FIG. 8A shows selection of one heart cycle at times Tn-1 to Tn. Thus, the time integral of the normalized surface integral of FIG. 7 is calculated over time Tn-1 to Tn.

The time integral is used to calculate an average surface integral of Doppler energy. The time integral of the normalized surface integral is normalized by time. In particular, the time integral is divided by the time period of integration, such as the number of frames of image plane data used to calculate the time integral of the normalized surface integral. Normalized time integrals of other parameters may also be calculated. Further, any calculation as a function of time for any parameter may be normalized by the time period.

Time periods derived from the normalized surface integral are also used to trigger various functions of the ultrasound system 100 or 400. For example, the beginning of the heart cycle triggers recording of echo signals in CINE 112, 182 or 408. The operator inputs a time period, as discussed above. The microprocessor 127 or 420 monitors the normalized surface integral waveform data for a reoccurrence of the selected begin point of the heart cycle. The microprocessor 127 or 420 then controls CINE 112, 182 or 408 to store data derived from echo signals until the end point is reached.

Various other quantities, other than those discussed above, are derived from the image plane data as instantaneous or period based calculations. Alternatively, acoustic or color value based ultrasound signal values are used to derive quantities. Other functions or other ultrasound parameter values could be used. For example, the average value of a parameter in a region of interest is calculated. Further, the area of the region of interest is also calculated. The average value or any other quantity is multiplied or divided by the area or a unit area to determine various quantities, such as volumetric flow (average velocity multiplied by area).

Other complex functions are also calculated, such as the product of energy and velocity. This product may predict the amount of blood flow in jets and may be of use in perfusion. Energy and velocity values associated with each particular pixel are added to create an energy-velocity product frame of image plane data. The surface integral calculation or any other calculations are performed on the energy-velocity product image plane data. Further quantities, such as the time integral, are also calculated. Thus, the combination of image plane data associated with different parameters prior to performing various calculations also results in useful information. Functions other than the product may be used to obtain the complex function image plane data.

Any of the calculations discussed above or below, including complex functions, are also derived from image plane data associated with a 3-dimensional display. For example, instead of a surface integral, a volume integral is calculated. The volume integral or any other quantity is normalized by volume or time. The region of interest determinations discussed above apply to selecting a three-dimensional region of interest.

Generally, the quantities discussed above are relative values. Various variables, such as the power of the ultrasound signal provided by the transducer 104, 430 and depth attenuation, affect the values in the image plane data. Likewise, quantities calculated as a ratio are also relative.

Quantities associated with multiple regions of interest 131 acquired simultaneously or sequentially are compared or combined. The microprocessor 127 or 420 combines various quantities or waveforms. The combination creates comparison data. Preferably, the various settings of the ultrasound system 100 or 400, such as gain, are the same for acquisition and processing of echo signals to create comparison data. For combination or comparison discussed above, a region of interest 131 comprises a single spatial location, an entire organ or a volume.

As an example of combination or comparison, two regions of interest 131 in a person's liver are selected with input from the operator. The image plane data from the two regions of interest 131 are compared to determine the relative amount of perfusion at a certain time. For example, the surface integral of energy is calculated for each region of interest 131. Each surface integral provides a measure of perfusion. A ratio of the two surface integrals is created. The relative amount of perfusion is indicative of an infarction. The ratio function based on values in the linear scale is equivalent to the difference function based on values in a log scale.

Another example of comparing or combining quantities is the combination of quantities associated with two regions of interest 131 in different parts of the body, such as contralateral organs. Contralateral organs include kidneys, breasts, and testicles. As a further example, the surface integral of Doppler energy from the different regions of interest 131 is determined as a function of time to create two waveforms. The two waveforms are combined as a ratio, or other function, into one waveform. Combining these or other quantities accounts for differing gain, frequency, or other signal properties when the echo signals are acquired and processed. Contralateral organs provide good comparisons. The organs have similar properties, so any abnormality in one organ is likely to be highlighted when compared to the same type of organ in the same body.

As another example, image plane data for one region of interest 131 acquired at a first time is compared with image plane data for another region of interest 131 acquired at a different time. Thus, image plane data from one region of interest is used as a constant for comparison or combination with a second region of interest 131. The portion of the body represented by the second region of interest 131 may be operated on or subject to an injection of some substance, such as a contrast agent. The time difference is seconds, hours or days apart.

Heart area comparisons are an example of a comparison of one region of interest at one time with a different region of interest at another time. One region of interest is selected to correspond to the left ventricle at the ventricle's largest size. The second region is selected to correspond to the left ventricle at the ventricle's smallest size. Alternatively, the microprocessor region of interest is used as it varies as a function of time. Generally, the second region of interest is enclosed within the first region of interest. The image plane data from the first region of interest 131 is used to calculate an area corresponding to the largest area value for the left ventricle. The image plane data from the second region of interest 131 is used to calculate an area corresponding to the smallest value for the left ventricle. Both areas are combined as a ratio, a product or some other function.

Surface and time integral quantities associated with a single region of interest acquired sequentially are also used for comparison or combination. For example, the first acquired quantity is used as a constant and compared or combined with the second quantity. The second quantity is derived from image plane data acquired after surgery or an injection, such as an injection of a contrast agent.

The times or time periods for calculating the sequential quantities are based on any desired event, such as heart cycle, time of washout of an injected contrast agent, or an arbitrary time. For example, the time period of calculation of a mean is set to a portion of a heart cycle, one heart cycle or multiple heart cycles. Image plane data is then acquired over the time period. The calculation is triggered by the microprocessor 127 or 420 based on an input, such as ECG leads and processor 137 or 403, or based on the surface integral as discussed above. The trigger prevents false weighting of any period based quantities.

A ratio of a quantity from a first time period to the quantity from another time period is obtained. For example, the average velocity for one cardiac cycle is combined as a ratio with the average velocity for another cardiac cycle. Further, the average velocities as a function of time for each cardiac cycle are combined as a ratio waveform.

Quantities derived from image plane data associated with one region of interest and the same period of time are also combined. For example, the mean of a parameter associated with the region of interest over the selected time period is determined. A high and low value over the selected time period are also determined. The high and low values are each divided by the mean. Further, the high verses low values, divided by the mean, are also combined as a ratio. For example, the highest velocity for a region of interest over the selected time period as a function of the mean is compared or combined with the lowest velocity for a region of interest over the selected time period as a function of the mean.

Quantities associated with different parameters for the same region of interest 131 taken at the same time are also used for comparison or combination. For example, a Doppler energy surface integral and a B-mode intensity surface integral for a region of interest are computed. A waveform for each computed value as a function of time is also created. Further, a waveform of the ratio of these computed values is generated.

This particular Doppler energy to B-mode intensity ratio is indicative of the amount of blood compared to tissue. Since the amount of tissue is invariant, the ratio is used to determine the amount of blood at any give time, such as over a cardiac cycle. Any of the singular or multiple region of interest 131 comparisons and combinations described above and below could also be based on a comparison or combination quantities derived from different parameters.

Instead of using a ratio, other functions for combining the quantities may be used, such as product functions to create the comparison data. Further, any of the various quantities, such as surface integrals, means, areas or time integrals, can be combined. Other ultrasound parameters, or types of signals, can also be used, such as variance, velocity, energy, B-mode intensity or others. Any of the various comparison data can be created as a function of time. Thus, a waveform of comparison data is created.

A ratio metric comparison tends to cancel out differences due to gain, angle dependence, level of fluid and other differences to provide more accurate results. Further, any differences between the settings of the ultrasound system 100 or 400 while acquiring echo signals, such as differing gain, frequency, transmit power or bandwidth, are preferably corrected prior to any calculations. These differences are available since the ultrasound system 100 or 400 uses the gain, frequency, transmit power and bandwidth to obtain the image plane data. The frequency and bandwidth are scaled, and the gain and transmit power are logarithmically adjusted.

Multiple regions of interest 131 are also selected to remove depth dependent attenuation. The regions of interest 131 are selected to have comparable depths. The operator subjectively selects multiple regions of interest 131 with approximately the same depth position in the image 130. Comparable depth regions of interest 131 are generally easily selected in the same organ or contralateral organs. Thus, depth dependent attenuation is removed by the selection of regions of interest 131 in the same organ or contralateral organs. Quantities associated with volume regions of interest may also be combined or compared as discussed above.

Selection of regions of interest 131, any of the various combinations, calculations, waveforms or other processing are also performed using CINE playback. CINE 112, 182 or 408 plays back Doppler and B-mode data. CINE 112, 182 or 408 records the data used to create multiple frames of image plane data over a time period, such as ten (10) seconds.

Using CINE 112, 182 or 408, a particular frame of image plane data is played back multiple times for quantification and comparison. The CINE 112, 182 or 408 also allows for creation of more stable values for the image plane data by allowing adjustment of the region of interest 131 or of any threshold for rejection of undesirable data. The time period, including beginning points and end points, are also adjusted using CINE playback. Icons or margins are positioned on either a waveform or frame count to designate the beginning and ending points of the time period.

For example, a different threshold for determination of a microprocessor region or regions of interest 302 is applied. The quantities and waveforms derived from the new microprocessor regions of interest 302 for the same frame or frames of image plane data are calculated, such as the surface integral of Doppler energy. Different data stored within CINE 112, 182 or 408 could also be selected for various calculations, including contiguous or non-contiguous time frames for the same or different regions of interest 131.

Referring to FIGS. 1 and 15, any of the various quantities, waveforms, regions of interest 131 and histograms discussed above are displayed on display unit 132 or 440. The various information for display is created as either as part of CINE 112, 182 or 408 playback or in real-time. The microprocessor 127, 420 has an output to graphics memory unit 129, 462, as represented by block 127f (FIG. 1). Graphics memory unit 129, 462 provides information to combining unit 124, 463. Combining unit 124, 463 combines the microprocessor 127, 420 output with the appropriate image 130 for display on display unit 132, 440. For example, the average linear B-mode intensity is displayed on display unit 132.

As shown in FIG. 9, the quantity calculated for the time integral of the normalized surface integral of Doppler energy is displayed on the screen of display unit 132 in box 250. Other calculated values could also be displayed in box 250. Multiple quantities and waveforms are displayed simultaneously.

Waveforms, such as the normalized surface integral of Doppler energy as a function of time, are displayed as shown in FIG. 8A. The waveforms are displayed with the image 130 and box 250.

A profile curve of ultrasound signal values as a function of spatial location is displayed. The profile is displayed in conjunction with selection of a line 272 as the region of interest 131.

The data associated with histograms 200, two-dimensional histograms 216 or three-dimensional histograms are also displayed as a waveform. The waveform comprises the bin data as a function of the bin ultrasound values. Furthermore, the histograms are displayed before or after any alteration, such as converting to a linear scale.

The bin data and bin ultrasound values of the two-dimensional histogram 216 are displayed as a series of curves or as a three dimensional graph. For the series of curves display, each curve corresponds to a particular bin ultrasound value along one dimension. Three-dimensional histograms are displayed as a series of two-dimensional histogram displays.

Displaying waveforms and quantities derived from different regions of interest 131 or at different times allows users to compare the waveforms and quantities. The various comparisons or combinations discussed above, either as quantities or waveforms, are displayed. Different regions of interest 131 or time periods for the same region of interest 131 are selected as discussed above. For example, different regions of interest 131 or time periods are selected during multiple CINE 112, 182, 408 playback of echo signals. The waveform and quantity data is stored. Once all the waveforms and quantities are calculated, a comparison of the waveforms and quantities derived from the first region of interest 131 or time period to the subsequent region of interest 131 or time period is displayed.

The waveforms, calculations and other information displayed as discussed above is updated once per frame displayed on display unit 132. A moving average of the various waveforms and quantities is created for time period based quantities or waveforms. The moving average is obtained by overlapping the integration interval for successive measurements. Alternatively, the waveforms, calculations and other information may be updated at the end of any interval, such as every heart cycle or any other time period.

The display of particular waveforms and calculations in one or more time periods could also be based on a comparison of image plane data, quantities, waveforms or combinations of the image plane data. For example, a surface integral quantity associated with the time period with the greatest surface integral quantity is displayed. As another example, the frames of Doppler energy image plane data within a time period with the highest velocity value are displayed.

Other than display, various quantities are used to control the ultrasound system 100, 400. The microprocessor 127, 420 controls various internal processes or outputs control signals on line 138, 421 based on the quantities. For example, a depth gain compensation automatic adjustment is provided. The mean B-mode intensity for a region of interest 131 is calculated. The mean is calculated as discussed above, or any other method. Another mean B-mode intensity for the same region of interest 131 at a different time or for a different region of interest 131 is calculated. If the means are different, then the image plane data associated with one of the regions of interest 131 or times is altered by changing the operation of the beamformer 102, 402 to yield an equal mean.

Alternatively, high order quantities may be examined for bell curve distribution. If the quantity is not distributed as a bell curve, the image plane data is altered to yield a bell curve. Altering the image plane data compensates for differing gains. Other internal processes could be controlled by the microprocessor 127, 420 based on various quantities.

As another example of control based on quantities, injection of contrast agents is controlled. A calculation is performed that changes over time based on events, such as decay of a contrast agent. For decay of contrast agent, the mean B-mode intensity or surface integral of Doppler energy is calculated. Once the mean or surface integral reaches a particular low value, the microprocessor 127, 420 outputs a control signal on line 138, 421. The control signal is used by an external device, such as an injection pump, to trigger particular operations. For example, the injection pump injects more contrast agent based on the control signal. Other external devices may be controlled by the microprocessor 127, 420. Formation of an ice ball for cryogenics may be monitored and controlled. Various quantities associated with various calculations may be used to trigger the control signal.

Figure 1B:
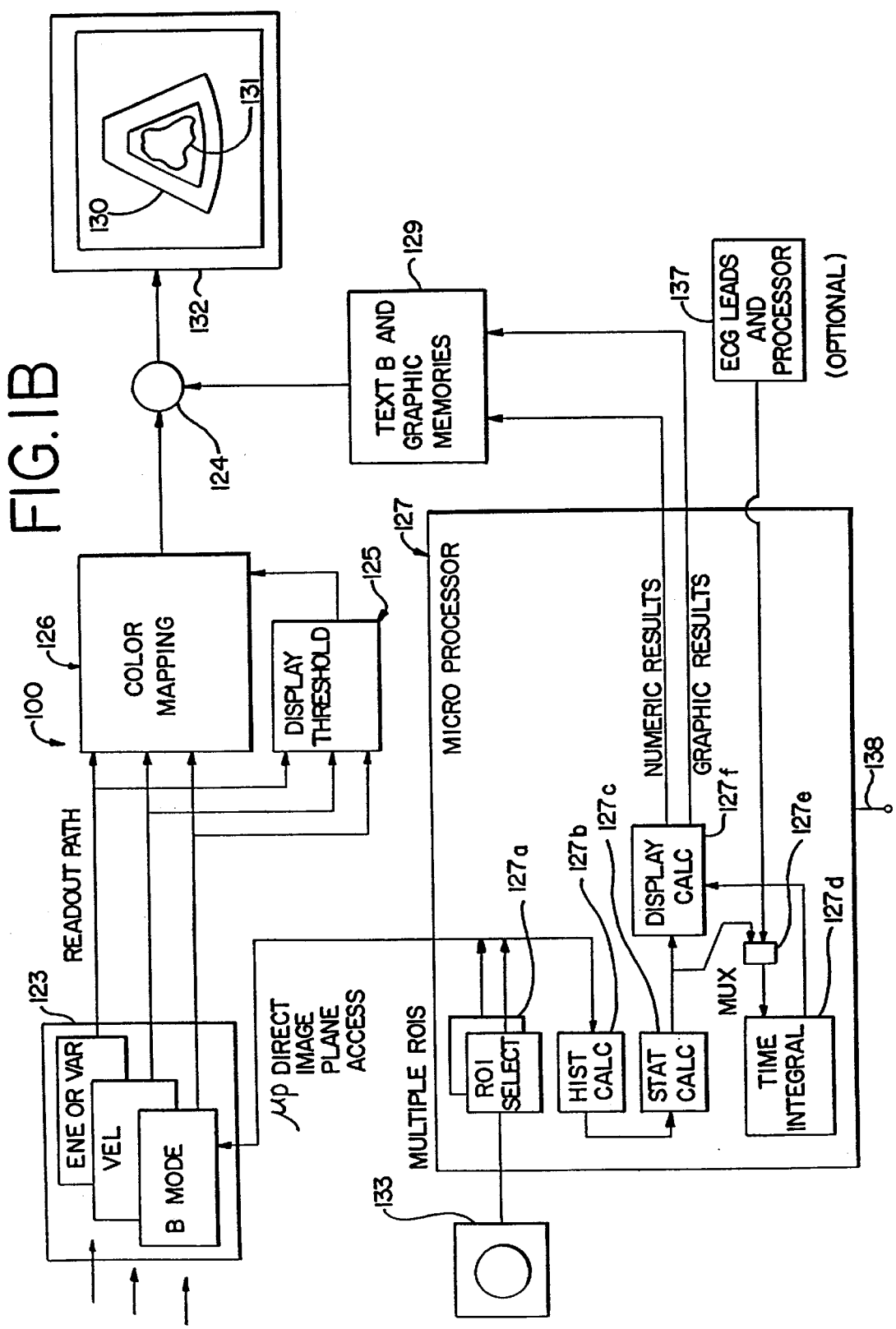

Either the embodiment of FIGS. 1A and 1B, the embodiment of FIGS. 15A and 15B, or other embodiments are capable of using various aspects of the above described invention. While the invention has been described above by reference to various embodiments, it will be understood that different changes and modifications can be made without departing from the scope of the invention.

It is therefore intended that the foregoing detailed description be understood as an illustration of the presently preferred embodiments of the invention, and not as a definition of the invention. It is only the following claims, including all equivalents, that are intended to define the scope of this invention.

We claim:

1. A method of providing flow quantity data by thresholding in an ultrasonic apparatus comprising the steps of:
    acquiring a Doppler energy for each of multiple spatial locations in a region of interest at a first time;
    acquiring a Doppler velocity for each of said multiple spatial locations in said region of interest at said first time;
    applying a threshold to said Doppler energies based on the Doppler velocities to obtain remaining Doppler energies; and
    summing said remaining Doppler energies.

2. The method of claim 1, said thresholding step comprising the steps of:
    determining said threshold as a Doppler velocity cut-off value; and
    setting the Doppler energy to zero for each of said multiple spatial locations where the Doppler velocity is below the Doppler velocity cut-off value.

3. The method of claim 1 further comprising displaying said sum.

4. The method of claim 3, the step of displaying comprising the step of displaying a waveform of said sum as a function of time.

5. The method of claim 1 wherein the steps of acquiring said Doppler energy for each of said multiple spatial locations in said region of interest at said first time and acquiring said Doppler velocity for each of said multiple spatial locations in said region of interest at said first time comprise acquiring values for each of multiple spatial locations in a volume region of interest.

6. The method of claim 1 wherein the step of applying said threshold to said Doppler energies based on said Doppler velocities comprises applying a histogram.

7. The method of claim 1 wherein the step of summing said remaining Doppler energies to obtain said sum comprises applying a histogram.

8. An ultrasound apparatus for providing flow quantities by applying a threshold comprising:
    a buffer for storing Doppler energy and Doppler velocity data for each of multiple spatial locations in a region of interest;
    a threshold value data;
    a microprocessor for applying said threshold data to said Doppler velocity data to remove Doppler energy data associated with Doppler velocities below said threshold value data and for summing the remaining of said Doppler energy data.

9. The ultrasound apparatus of claim 8 further comprising a display device including display associated with said sum data.

* * * * *

UNITED STATES PATENT AND TRADEMARK OFFICE
CERTIFICATE OF CORRECTION

PATENT NO.    : 6,241,677 B1
DATED         : June 5, 2001
INVENTOR(S)   : Ismayil M. Guracar It is certified that error appears in the above-identified patent and that said Letters Patent is hereby corrected as shown below:

<u>Title page,</u>
Item [12], delete "et al.".
Item [75], delete "; Samuel H. Maslak, Woodside; John W. Allison, Sunnyvale; Paul E. Chandler, Santa Cruz; John L. Jackson, Menlo Park; Arvind Jain, San Jose; Laurence S. McCabe, Sunnivale, all of CA" and substitute -- , CA -- in its place.

Item [56], References Cited, U.S. PATENT DOCUMENTS, delete "Linuma" and substitute -- Iinuma -- in its place. (two occurrences)
OTHER PUBLICATIONS, delete "Quantative" and substitute -- Quantitative -- in its place.
Delete "Railo" and substitute -- Radio -- in its place.
Delete "jpn" and substitute -- Jpn -- in its place.
Delete "Continous" and substitute -- Continuous -- in its place.
Delete "Frequncy" and substitute -- Frequency -- in its place.
Delete "Medicine" and substitute -- Medical -- in its place.

<u>Column 5,</u>
Line 15, insert -- an -- before "ultrasound".

<u>Column 7,</u>
Line 1, delete "FIG. 1," and substitute -- FIG. 11, -- in its place.

<u>Column 22,</u>
Line 57, delete "(ij,k)" and substitute -- (i, j, k) -- in its place.

<u>Column 23,</u>
Line 37, delete "10".

UNITED STATES PATENT AND TRADEMARK OFFICE
CERTIFICATE OF CORRECTION

PATENT NO.     : 6,241,677 B1
DATED          : June 5, 2001
INVENTOR(S)    : Ismayil M. Guracar It is certified that error appears in the above-identified patent and that said Letters Patent is hereby corrected as shown below:

<u>Column 30,</u>
Line 54, after "including" insert -- a --.

Signed and Sealed this

Twenty-ninth Day of October, 2002

Attest:

Attesting Officer

JAMES E. ROGAN
*Director of the United States Patent and Trademark Office*